(12) United States Patent
Sebti et al.

(10) Patent No.: US 7,632,805 B2
(45) Date of Patent: Dec. 15, 2009

(54) GROWTH FACTOR BINDING MOLECULES

(75) Inventors: Said Sebti, Tampa, FL (US); Andrew D. Hamilton, Guilford, CT (US)

(73) Assignees: University of South Florida, Tampa, FL (US); Yale University, New Haven, CT (US)

( * ) Notice: Subject to any disclaimer, the term of this patent is extended or adjusted under 35 U.S.C. 154(b) by 0 days.

(21) Appl. No.: 11/226,112

(22) Filed: Sep. 14, 2005

(65) Prior Publication Data

US 2006/0084596 A1 Apr. 20, 2006

Related U.S. Application Data

(63) Continuation of application No. 09/811,945, filed on Mar. 21, 2001, now Pat. No. 7,157,419.

(60) Provisional application No. 60/190,938, filed on Mar. 21, 2000.

(51) Int. Cl.
*C07K 5/10* (2006.01)

(52) U.S. Cl. .................. 514/2; 514/9; 514/18; 514/717; 514/721; 530/330; 568/584; 568/585; 568/586

(58) Field of Classification Search ........................ None
See application file for complete search history.

(56) References Cited

U.S. PATENT DOCUMENTS

| 5,457,113 A * | 10/1995 | Cullinan et al. ............. 514/319 |
| 5,770,380 A | 6/1998 | Hamilton et al. |
| 6,262,257 B1 | 7/2001 | Gale et al. |
| 2003/0118589 A1 | 6/2003 | Sebti et al. |
| 2005/0197401 A1 | 9/2005 | Sebti et al. |

FOREIGN PATENT DOCUMENTS

| WO | WO 01/70930 A2 | 9/2001 |
| WO | WO 03/059925 A1 | 7/2003 |
| WO | WO 2005/072779 A2 | 8/2005 |

OTHER PUBLICATIONS

Hagedom et al. "A Short Peptide Domain of Platelet Factor 4 Blocks Angiogenic Key Events Induced by FGF-2" The FASEB Journal. vol. 15, Mar. 2001, pp. 550-552.*
Bawa et al. 'A Single Amion Acid Substitution in MSH5 Results in DNA Alkylation Tolerance' Gene. vol. 315, 2003, pp. 177-182.*
Rudinger, J. (1976). Peptide Hormones (ed. J.A. Parsons). University Park Press. Baltimore. pp. 1-7.*
Dermer, Gerald. "Another Anniversary for the War on Cancer." Bio/Technology, vol. 12. Mar. 1994.*
Gura, Trisha. "Systems for Identifying New Drugs are Often Faulty." Science, vol. 278, pp. 1041-1042. Nov. 1997.*
Golden, Fredrick. "Of Mice and Men: Don't Blame the Rodents" Time, pp. 26. May 18, 1998.*
Veggeberg, Scott. 'Fighting Cancer With Angiogenesis Inhibitors' The Scientist, vol. 16, No. 11, May 2002, pp. 1-5. accessible via "http://www.the-scientist.com".*
Black, Harvey 'Angiogenesis—Promoting and Blocking—Comes Into Focus' The Scientist, vol. 12, No. 9, Apr. 1998, pp. 1-4. Accessible via "http://www.the-scientist.com".*
Hogquist et al. "T Cell Receptor Antagonist Peptides induce postivie selection," Cell, Cell Press Cambridge, NA, US, vol. 76, No. 1. Jan. 1994, pp. 17-27.*
Bradely et al. "Limits of Cooperativeity in a Structurally Modular Protein: Response of the Notch Ankyrin Domain to Analogus Alanine Substitutions in Each Repeat." J. Mol. Biol. vol. 324, 202, pp. 373-386.*
Andersson, M. et al. "Involvement of loop 2 of platelet-derived growth factor-AA and -BB in receptor binding" *Growth Factors*, 1995, 12:159-164.
Bergers, G. et al. "Benefits of targeting both pericytes and endothelial cells in the tumor vasculature with kinase Inhibitors" *J Clin Invest*, 2003, 111:1287-1295.
Dvorak H.F. et al. "Vascular permeability factor/vascular endothelial growth factor and the significance of microvascular hyperpermeability in angiogenesis" *Curr Top Microbiol Immunol*, 1999, 237:97-132.
Dvorak, H.F. "Vascular permeability factor/vascular endothelial growth factor: a critical cytokine in tumor angiogenesis and a potential target for diagnosis and therapy" *J Clin Oncol*, 2002, 20:4368-4380.
Eriksson, U. and Alitalo, K. "Structure, expression and receptor-binding properties of novel vascular endothelial growth factors" *Curr Top Microbiol Immunol*, 1999, 237:41-57.
Ferrara, N. "Vascular endothelial growth factor: molecular and biological aspects" *Curr Top Microbiol Immunol*, 1999, 237:1-30.
Ferrara, N. "Role of vascular endothelial growth factor in physiologic and pathologic angiogenesis: therapeutic implications" *Semin Oncol*, 2002, 29:10-14.
Jain, R.K. "Tumor angiogenesis and accessibility: role of vascular endothelial growth factor" *Semin Oncol*, 2002, 29:3-9.
Kerbel, R.S. "Tumor angiogenesis: past, present and the near future" *Carcinogenesis*, 2000, 21:505-515.
Laird, A.D. et al. "SU6668 is a potent antiangiogenic and antitumor agent that induces regression of established tumors" *Cancer Res*, 2000, 60:4152-4160.
Lin, Q. et al. "Protein surface recognition by synthetic agents: Design and structural requirements of a family of artificial receptors that bind to cytochrome c" *Biopoly*, 1998, 47:285-297.
Lin, Q. and Hamilton, A. "Design and synthesis of multiple-loop receptors based on a calix[4]arene scaffold for protein surface recognition" *C.R. Chimie*, 2002, 5:441-450.
Miao, R.Q. et al. "Kallistatin is a new inhibitor of angiogenesis and tumor growth" *Blood*, 2002, 100:3245-3252.
Morin, M.J. "From oncogene to drug: development of small molecule tyrosine kinase inhibitors as anti-tumor and anti-angiogenic agents" *Oncogene*, 2000, 19:6574-6583.

(Continued)

*Primary Examiner*—Anish Gupta
(74) *Attorney, Agent, or Firm*—Saliwanchik, Lloyd & Saliwanchik

(57) ABSTRACT

Growth factor binding molecules having a plurality of peptide loops attached to a non-peptide organic scaffold, preferably having pseudo-six amino acid peptide loops with four amino acid sidechains. The growth factor binding molecules specifically bind various growth factors and are suitable for treating a subject having tumors or restinosis. In one embodiment a platelet-derived growth factor binding molecule is disclosed that is used to inhibit tumor growth and angiogenesis in solid tumors.

37 Claims, 16 Drawing Sheets

OTHER PUBLICATIONS

Oefner, C. et al. "Crystal structure of human platelet-derived growth factor BB" *Embo J*, 1992, 11:3921-3926.

Sebti, S. and Hamilton, A.D. "Design of growth factor antagonists with antiangiogenic and antitumor properties" *Oncogene*, 2000, 19(56):6566-6573.

Sun, J. et al. "Inhibiting angiogenesis and tumorigenesis by a synthetic molecule that blocks binding of both VEGF and PDGF to their receptors" *Oncogene*, 2005, 24:4701-4709.

Sun, J. et al. "Blocking angiogenesis and tumorigenesis with GFA-116, a synthetic molecule that inhibits binding of vascular endothelial growth factor to its receptor" *Cancer Res*, May 15, 2004, 64(10):3586-3592.

Sun, J. et al. "Inhibiting angiogenesis and tumorigenesis by a synthetic molecule that blocks binding of both VEGF and PDGF to their receptors" presented at Annual Meeting of the American Association for Cancer Research, Mar. 26-30, 2004, Orlando, FL, abstract No. 4533.

Wedge, S.R. et al. "ZD4190: an orally active inhibitor of vascular endothelial growth factor signaling with broad-spectrum antitumor efficacy" *Cancer Res*, 2000, 60:970-975.

Zhang, W. et al. "A monoclonal antibody that blocks VEGF binding to VEGFR2 (KDR/Flk-1) inhibits vascular expression of Flk-1 and tumor growth in an orthotopic human breast cancer model" *Angiogenesis*, 2002, 5:35-44.

International Search Report PCT/US01/08920, dated Aug. 31, 2001.

Bach, A.C. et al. "Structural studies of a family of high affinity ligands for GPIIb/IIIa" *J. Am. Chem. Soc.*, 1994, 116:3207-3219.

Blaskovich, M.A. et al. "Design of GFB-111, a platelet-derived growth factor binding molecule with antiangiogenic and anticancer activity against human tumors in mice" *Nature Biotech.*, 2000, 18:1065-1070.

Hamuro, Y. et al. "A calixarene with four peptide loops: an antibody mimic for recognition of protein surfaces" *Agnew. Chemie Int. Ed. Engl.*, 1997, 36:2680-2683.

Park, H.D. et al. "Protein surface recognition by synthetic receptors: a route to novel sub-micromolar inhibitors for chymotrypsin" *J. Am. Chem. Soc.*, 1999, 121:8-13.

Shuker, S.B. et al. "Solid-phase synthesis of a novel peptide substituted calyx[4]arene" *Synlett*, 2001, 2:210-213.

Wilson, I.A. et al. "Structural aspects of antibodies and antibody-antigen complexes" *Ciba Foundation Symp.*, 1991, 159:13-39.

* cited by examiner

O-4 Calix     O-3 Calix     But-Calix

Structure of GFB-114

8-acid

Structure of "DPM-2" compounds (GFB-128 through GFB-131)

Structure of "DPM-2" compounds (GFB-128 through GFB-131)

Structures of GFB-132 through GFB-137

GROWTH FACTOR BINDING MOLECULES

1. REFERENCES

The present application is a continuation of U.S. application Ser. No. 09/811,945, filed Mar. 21, 2001, now U.S. Pat. No. 7,157,419, which claims benefit of U.S. Provisional Application Ser. No. 60/190,938, filed Mar. 21, 2000, each of which is hereby incorporated by reference herein in its entirety, including any figures, tables, nucleic acid sequences, amino acid sequences, and drawings.

2. STATEMENT OF FEDERAL SUPPORT

The present invention is made in whole or in part with financial support from the Federal Government under grant CA78038 from the National Institutes of Health, National Cancer Institute, and United States Army grant DAMD17-99-1-9458. The Federal Government has certain rights in this invention.

3. FIELD OF INVENTION

The present invention relates generally to a family of synthetic molecules capable of binding to growth factors. More particularly, the invention relates to agents that bind growth factors through a plurality of peptide loops attached to a non-peptide, organic scaffold. The invention further relates to compositions comprising molecules that bind growth factors and their use in the treatment of mammals, where inhibition of cell growth and/or inhibition of angiogenesis are desirable, including the treatment of tumors and other diseases associated with hyper- or abnormal cell proliferation such as restenosis.

4. BACKGROUND

Vascular endothelial growth factor (VEGF), acidic fibroblast growth factor (aFGF), platelet-derived growth factor (PDGF), and insulin-like growth factor-1 (IGF-1) are active modulators of cell proliferation, with profound effects on tumor cell growth, and, in the case of PDGF, intimal smooth muscle cell growth. In addition, certain such growth factors stimulate blood vessel formation, or angiogenesis. Inhibition of angiogenesis is an important therapeutic goal in the control of tumor development in cancer patients.

Vascular disease treatment by balloon angioplasty, implantation of a stent, or by resection (e.g. a vascular graft), results in local damage to the endothelial cell lining of the vessel wall. A result of the damage is that the smooth muscle cells of the intima begin to proliferate in a PDGF-dependent process termed intimal hyperplasia or restenosis. Despite this side-effect, percutaneous transluminal coronary angioplasty, stent insertion, and vascular by-pass and grafting remain primary treatments for many patients with coronary artery disease and can relieve myocardial ischemia by reducing lumen obstruction and improving coronary flow. A very significant proportion of patients develop restenosis within three months. Restenosis results in significant morbidity or frequently necessitates further interventions such as repeat angioplasty or coronary bypass surgery.

Platelet-derived growth factor (PDGF) is a potent inducer of growth and motility in several cell types such as fibroblasts, endothelial cells and smooth muscle cells. It induces cell proliferation, angiogenesis, wound healing, chemotaxis and inhibits apoptosis. PDGF has also been directly implicated in malignant diseases involving uncontrolled cell proliferation such as cancer where overexpression of PDGF and/or PDGF receptors is common in human tumors including glioblastomas and sarcomas. In addition to its role in stimulating uncontrolled growth of cancer cells, PDGF also stimulates the proliferation and migration of endothelial cells leading to formation of new blood vessels, a process that is required for the growth of tumors. Furthermore, PDGF has also been shown to stimulate endothelial cells to express high levels of vascular endothelial growth factor (VEGF) a potent angiogenesis inducer. Finally, the importance of PDGF in angiogenesis has also been documented by the fact that mice deficient in PDGF-BB or its receptor β are defective in blood vessel development.

PDGF elicits the above biological response by binding to its cell surface receptor, PDGFR, a tyrosine kinase. Binding results in dimerization, receptor auto (cross) phosphorylation and recruitment via the resulting phosphotyrosine of SH2 domain-containing signaling proteins such as Grb2/SOS1, PLC-γ, PI-3kinase and Src. These proteins trigger several arms of the PDGF signal transduction pathways that are involved in different cellular responses. For example, Grb2/Sos1 activates the GTPase Ras which in turn results in the activation of a cascade of mitogen-activated protein kinases (MAPK), such as Erk1 and Erk2, and this contributes to the proliferation arm of the PDGF signaling pathway. Others such as PI3-kinase activate yet another kinase, AKT, which is responsible for the survival or the anti-apoptotic arm of PDGF signaling pathways.

The involvement of PDGF overactivity in several diseases with excessive proliferation prompted many researchers to target PDGF as a therapeutic strategy. The approaches that have been used to interfere with aberrant PDGF function in disease include PDGFR antibodies that block PDGF binding, linear or cyclic peptides corresponding to areas of PDGF that bind its receptor, receptor dimerization antagonists, and inhibitors of the tyrosine kinase activity of the receptor. An area that has been underexploited in the search of antagonists of PDGF overactivity is that of rationally designed agents that bind to PDGF and prevent it from activating its receptor. In this area only a few strategies such as antibodies against PDGF, soluble forms of PDGFR and DNA aptamers have been tried and those have had only marginal success. This is primarily due to the difficulty of designing agents to disrupt protein-protein interactions that are mediated over large surface binding areas, and because such molecules are often swiftly degraded by enzymes.

An attractive approach to producing synthetic molecules capable of binding to defined biological targets, involves synthetic antibody mimics disclosed by Hamilton and Yoshitomo in U.S. Pat. No. 5,770,380, issued Jun. 23, 1998, and which is hereby incoporated in its entirety by reference. Such molecules have the advantages of biological stability and can be rationally designed and screened. However, no such antibody mimics have previously been produced that specifically bind growth factors.

Here we describe a novel approach that targets growth factor surfaces, such as the regions of PDGF (loops I and III) that are involved in binding to its receptor, to overcome the aforementioned limitations in the art. These advantages and more will be apparent to those of skill in the art upon reading the following disclosure.

5. SUMMARY OF THE INVENTION

It is therefore an object of the present invention to provide growth factor binding compounds having a central non-peptide organic scaffold, such as a calix[4]arene, to which are attached two or more peptide loop domains. The peptide loop component is preferably based on a cyclic hexapeptide in which two residues are replaced by a 3-aminomethyl benzoate dipeptide mimetic containing a 5' amino substituent for attachment to the scaffold. In certain embodiments, the resulting molecules contain a functionalized and variable surface approximately 500 Å$^2$ (square Angstroms) in area. Such compounds are hereinafter referred to as growth factor binding molecules or agents.

It is a further object of the present invention to provide a growth factor binding molecule having an organic scaffold that is a calix[4]arene structure with specificity for binding to platelet derived growth factor, vascular endothelial growth factor, or acidic fibroblast growth factor, insulin-like growth factor 1.

It is a further object of the present invention to provide a composition for inhibiting cellular proliferation in a subject in need thereof, the composition comprising a pharmaceutically acceptable salt of a growth factor binding molecule of the present invention.

It is a further object of the present invention to provide a composition for treatment of a subject with excessive angiogenesis, in a subject in need thereof, the composition comprising a pharmaceutically acceptable salt of a growth factor binding molecule of the present invention.

It is a further object of the present invention to provide a method of treatment of a subject that has a tumor, the method comprising in a subject in need thereof, the composition comprising a pharmaceutically acceptable salt of a growth factor binding molecule of the present invention, wherein the effective amount inhibits growth of the tumor.

It is still a further object of the present invention to provide a method for measuring the amount of platelet-derived growth factor in a sample comprising obtaining a fluid sample, contacting the fluid sample with a growth factor binding molecule of the present invention and detecting the binding of the growth factor to the growth factor binding molecule of the present invention.

It is yet a further object of the present invention to provide a method for the delayed release of a platelet derived growth factor in a subject, the method comprising administering to the subject a stoichiometric complex of the growth factor and the growth factor binding molecule of the present invention.

It is yet a further object of the present invention to provide a means and composition for treating, inhibiting, or preventing restonosis or hyperplasia in a subject in need thereof, the composition comprising a pharmaceutically acceptable salt of a growth factor binding molecule of the present invention.

6. BRIEF DESCRIPTION OF THE DRAWINGS

7. DETAILED DESCRIPTION OF SELECTED DRAWINGS

Figure 1:
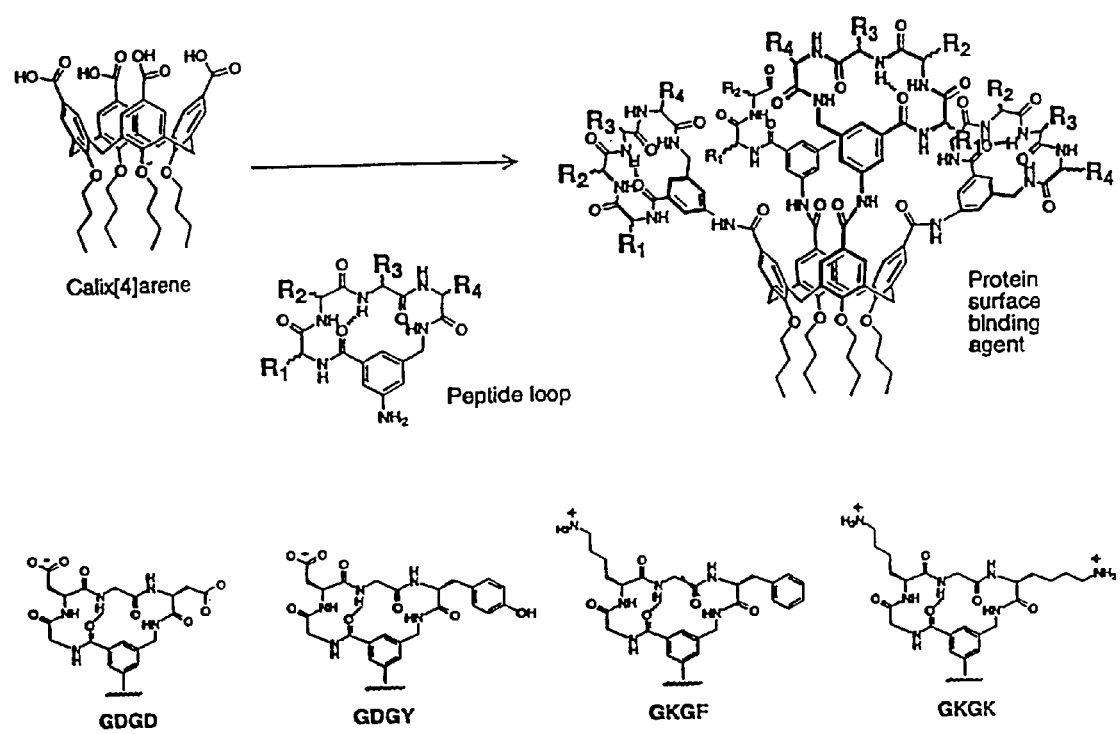
FIG. 1 illustrates the structure of embodiments growth factor binding (GFB) molecules.

FIG. 1 illustrates the structure of embodiments of growth factor binding compounds.

Figure 2:
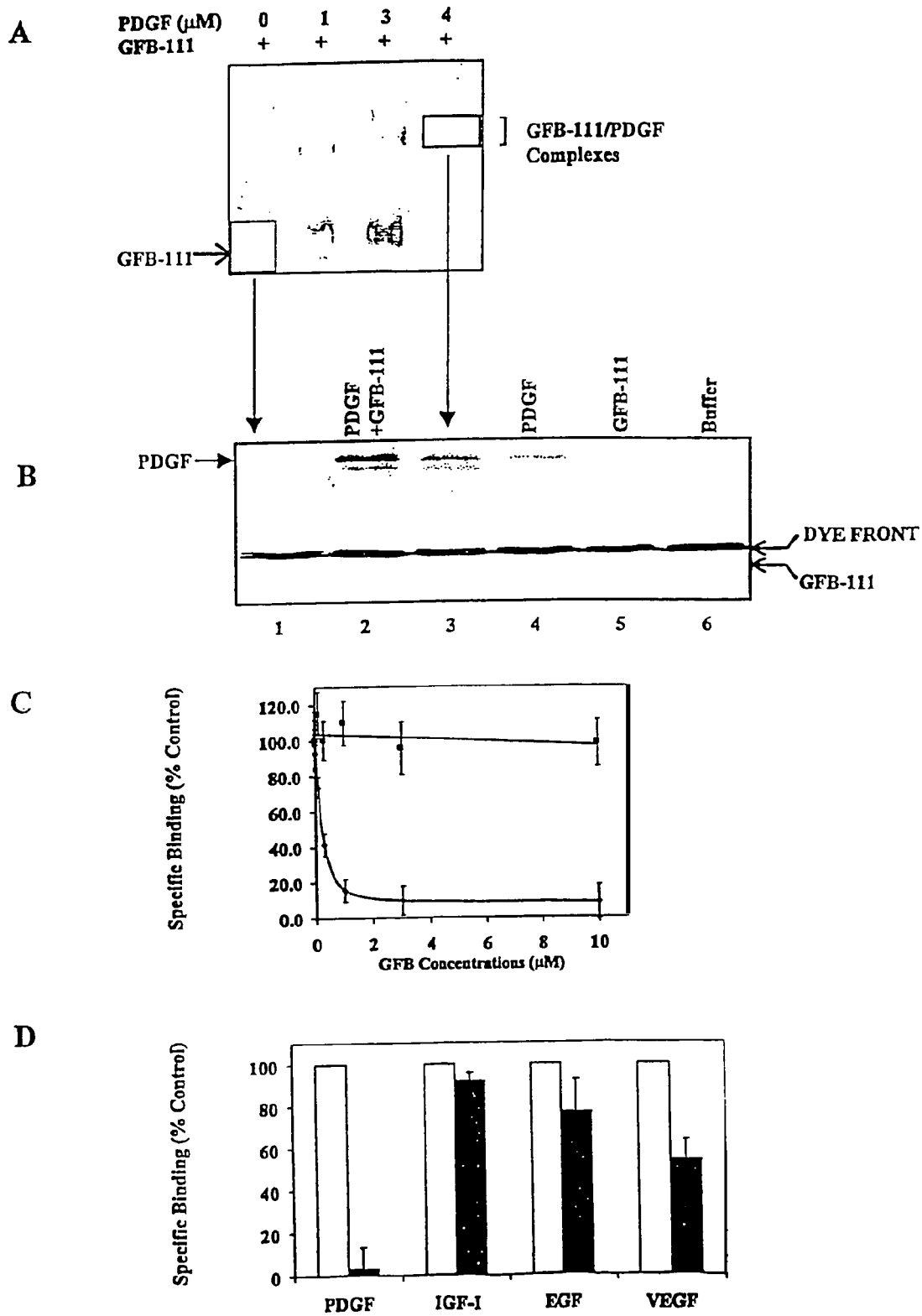
FIGS. 2A & 2B illustrate the binding of GFB-111 to platelet derived growth factor and other growth factors known to be involved in aberrant cell growth and proliferation.
FIGS. 2C & 2D illustrate GFB-111 inhibition of [$^{125}$I]-PDGF binding to its receptor on NIH3T3 cells.

FIGS. 2A and 2B illustrate the binding of GFB-111 to PDGF. GFB-111 is incubated with increasing concentrations of PDGF-BB and the mixtures are then loaded onto native PAGE. Bands corresponding to the boxed area are cut out of the lanes of the gel, denatured with SDS-PAGE loading buffer, loaded onto a 4% SDS-PAGE gel and silver stained as described under Methods. Lanes 1-6 correspond to GFB-111 from the native gel; PDGF+GFB-111 standards; GFB-111/PDGF complex from the native gel; PDGF standard; GFB-111 standard and buffer, respectively. Data are representative of three independent experiments.

FIGS. 2C and 2D illustrate GFB-111 inhibiting [$^{125}$I]-PDGF binding to its receptor on NIH 3T3 cells. NIH 3T3 (PDGF) or NIH 3T3 cells overexpressing either EGFR (EGF), IGFR (IGF) or Flk-1 (VEGF), are incubated with [$^{125}$I]-PDGF, [$^{125}$I]-EGF, [$^{125}$I]-IGF or [$^{125}$I]-VEGF, respectively and increasing concentrations of GFB-111 (♦) (C and D) or GFB-116 (■) (C). Cells are incubated at 4° C. degrees for 1-3 hours and washed 3 times with PBS and three times with Tris 25 mM pH 8.0, 1% TX-100, 10% Glycerol, 1% SDS. Lysates plus wash are counted. Excess of cold growth factors is used to obtain non-specific binding levels. Data are representative of three independent experiments.

Figure 3:
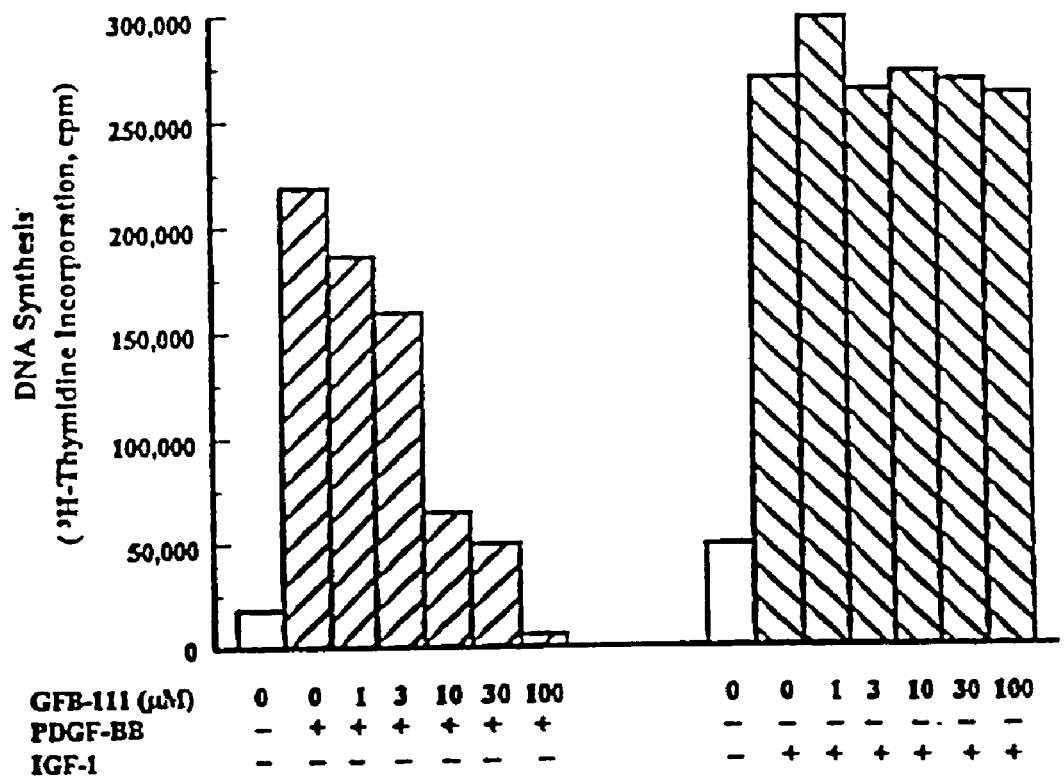
FIG. 3 illustrates GFB-111 selectively inhibits PDGF-stimulated receptor tyrosine autophosphorylation and activation of MAPK.

FIG. 3 illustrates the manner in which GFB-111 inhibits selectively PDGF-stimulated receptor tyrosine autophosphorylation and activation of MAPK. A. Starved NIH 3T3 cells (PDGF-BB and PDGF-AA), NIH 3T3 cells overexpressing either EGFR (EGF) or Flk-1 (VEGF) are pre-treated with GFB-111 before stimulation with PDGF-BB, PDGF-AA, EGF and VEGF. Cell lysates are run on SDS-PAGE gels, then transferred to nitrocellulose and Western blotted with anti-phosphotyrosine (4G10) or anti-phosphorylated Erk1/Erk2 (New England Biolabs). B. Starved NIH 3T3 cells (PDGF-AA, PDGF-BB, aFGF, bFGF), NIH 3T3 cells overexpressing EGFR, IGF-1R or Flk-1 and the human breast carcinoma SkBr3 that overexpresses ErbB2 (HRGβ) are pretreated with GFB-111 (100 µM) for 5 min before 10 min stimulation with the indicated growth factors as described under Methods. Cells lysates are then immunoblotted with anti-phospho Erk1/Erk2 as described for A. Data are representative of 3 independent experiments.

Figure 4:
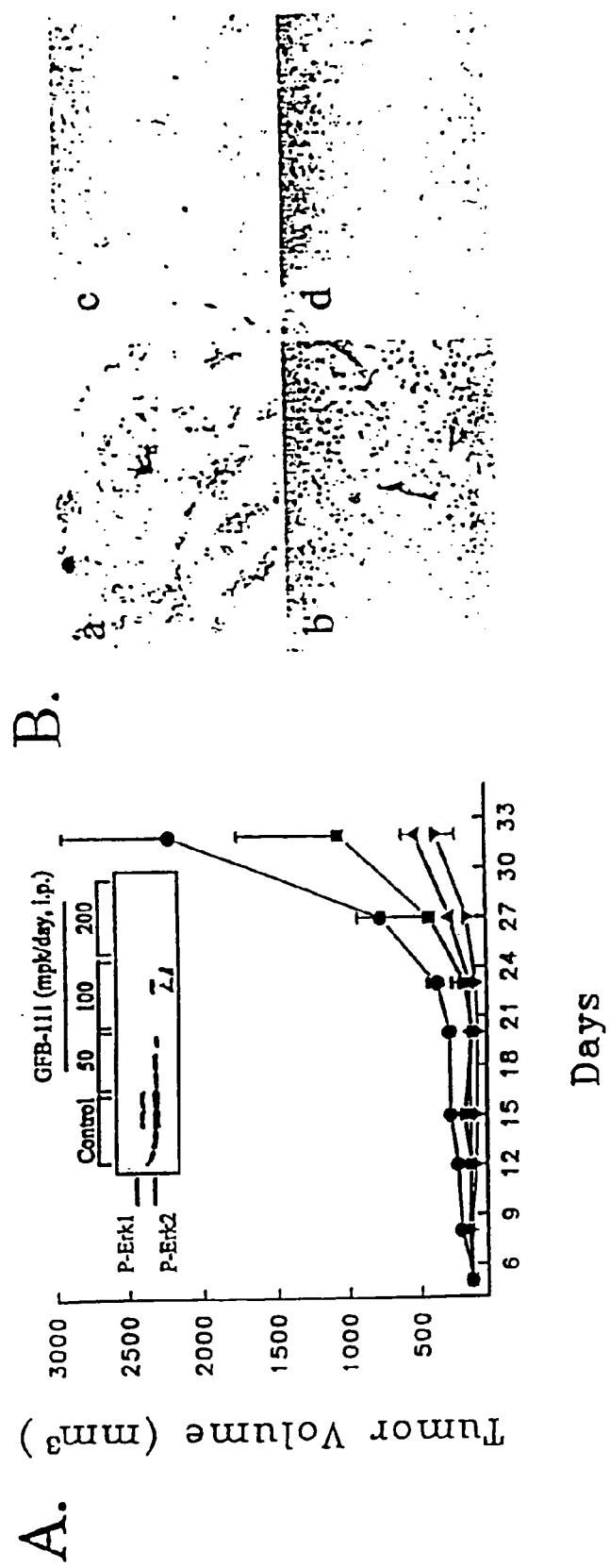
FIG. 4 illustrates GFB-111 selectively inhibits PDGF-stimulated DNA synthesis.

FIG. 4 illustrates GFB-111 selectively inhibiting PDGF-stimulated DNA synthesis. Starved NIH 3T3 or NIH 3T3 overexpressing IGFR are treated with GFB-111 and either PDGF or IGF-1, respectively, then labeled with $^3$H-thymidine. Cells are then washed, lysed and spotted onto glass fiber filters and $^3$H-thymidine incorporation quantified by scintillation counting as described under Methods. Data are representative of 3 independent experiments.

Figure 5:
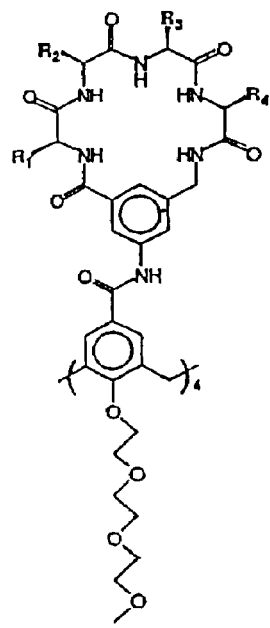
FIG. 5 illustrates GFB-111 inhibits tumor growth and angiogenesis in nude mice.
Figure 5:
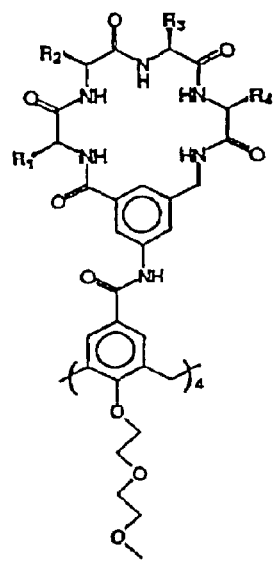
Figure 5:
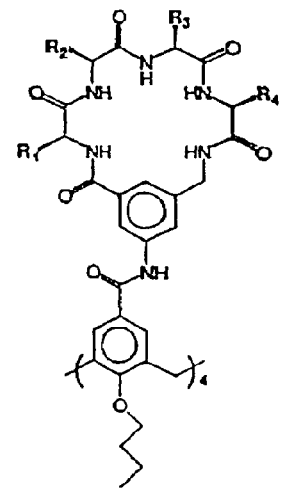

FIG. 5 illustrates GFB-111 inhibiting tumor growth and angiogenesis in nude mice. A. GFB-111 inhibits the growth of the human glioblastoma U87MG in nude mice. U87MG cells are injected s.c. into nude mice and when tumors reached about 100 mm$^3$, animals are dosed i.p. with 0.2 ml once daily. Control animals received a saline vehicle whereas treated animals are injected with GFB-111 (50, 100 or 200 mg/kg/day). The tumor volumes are determined as described under Methods, infra. For detection of phosphorylated/activated Erk1/Erk2 in tumors in vivo, the tumors are extracted, rinsed and tissumized in HEPES lysis buffer as described under Methods, infra. The lysates (50-100 ug) are electrophoresed on a 15% SDS-PAGE, transferred to nitrocellulose membranes and immunoblotted, with anti-phopho-p44/p42 MAPK (Thy202/Tyr204). Data are representative of 3 independent experiments. B. GFB-111 inhibits angiogenesis. On the indicated termination day of each experiment, the tumors are extracted as described under Methods. Four micrometer-thick tissue sections are obtained from the paraffin blocks and stained with hematoxylin and eosin (H&E) using standard histologic techniques. Tissue sections are also subjected to immunostaining for Factor VIII using the avidin biotin peroxidase complex technique. Rabbit polyclonal FVIII antibody is used at 1:400 dilution, following microwave antigen retrieval. Data are representative of two independent experiments.

BRIEF DESCRIPTION OF THE SEQUENCES

SEQ ID NO. 1 is the tetra-peptide GDFD.
SEQ ID NO. 2 is the tetra-peptide GDDD.
SEQ ID NO. 3 is the tetra-peptide d-ADGD (in which the alanine is in the D conformation, other amino acids being in the L conformation).
SEQ ID NO. 4 is the tetra-peptide GDLD.
SEQ ID NO. 5 is the tetra-peptide GDAD.
SEQ ID NO. 6 is the tetra-peptide GDGY.
SEQ ID NO. 7 is the tetra-peptide ADGD.
SEQ ID NO. 8 is the tetra-peptide GDSD.
SEQ ID NO. 9 is the tetra-peptide GKGF.
SEQ ID NO. 10 is the tetra-peptide GKGK.
SEQ ID NO. 11 is the tetra-peptide GDND.
SEQ ID NO. 12 is the tetra-peptide PDGD.
SEQ ID NO. 13 is the tetra-peptide GDDG.
SEQ ID NO. 14 is the tetra-peptide GDDY.
SEQ ID NO. 15 is the tetra-peptide GFGD.
SEQ ID NO. 16 is the tetra-peptide GDGD.
SEQ ID NO. 17 is the tetra-peptide D-2-NalDGD.
SEQ ID NO. 18 is the tetra-peptide D-2-AbuDGD.

8. DETAILED DESCRIPTION OF THE INVENTION

The agents disclosed herein bind growth factors. For example, in a specific embodiment, the growth factor to which an agent of the present invention binds is platelet derived growth factor (PDGF), and binding inhibits: activation of the PDGF receptor; stimulation of PDGF receptor tyrosine phosphorylation; activation of MAP kinase; tumor growth; and angiogenesis. Certain of these results are described by Blaskovich, M. A., et al. (2000) "Design of GFB-111, a platelet-derived growth factor binding molecule with antiangiogenic and anticancer activity against human tumors in mice," Nature Biotechnology, Vol. 18, pp. 1065-1070, which is hereby incorporated in its entirety by reference.

Figure 8:
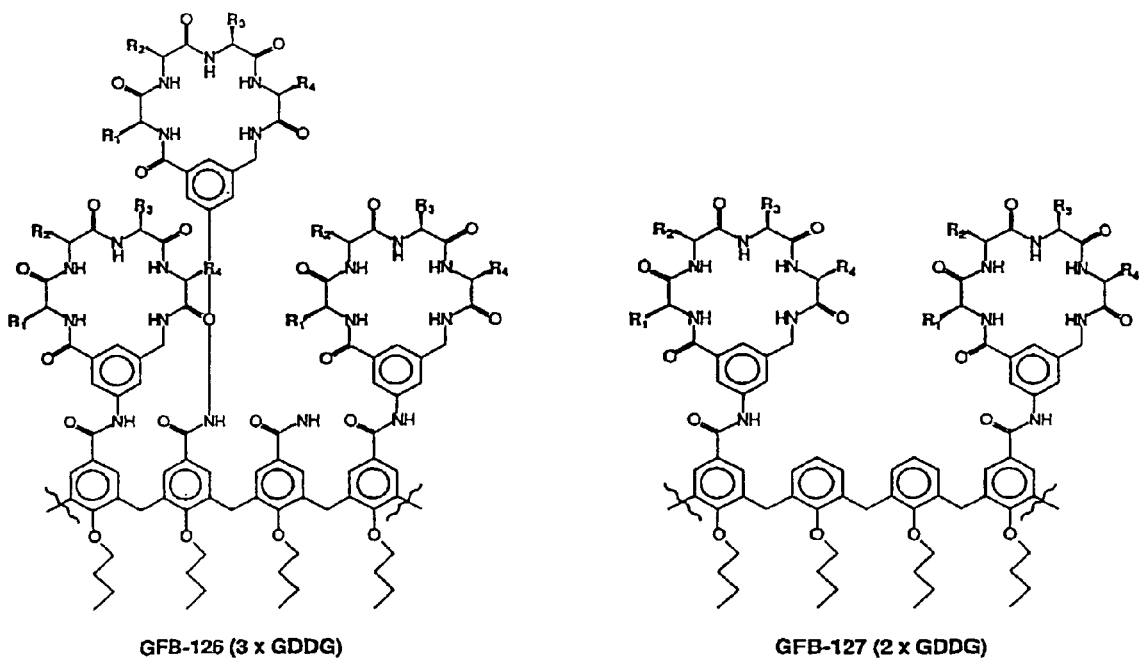
FIG. 8 illustrates the structures of GFB-124.
Figure 10:
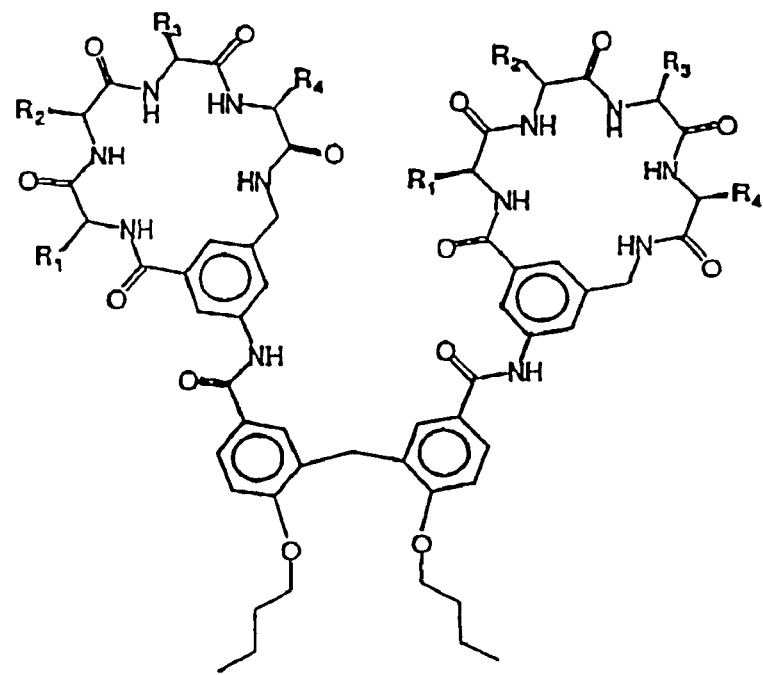
FIG. 10 illustrates the structure of "DPM-2" compounds (GFB-128 through GFB-131).

The growth factor binding molecules of the present invention comprise a plurality of peptide loops attached to a non-peptide, organic scaffold. As used herein, the term "organic scaffold" is understood to mean a carbon-containing molecule capable of attachment to a plurality of peptide loops such that peptide loops so attached are substantially available to bind to a target compound, such as a growth factor, and the plurality of said loops thereby form a portion of the molecule capable of binding to a growth factor. In preferred embodiments, the organic scaffold is capable of binding 2, 3, or 4 peptide loops, which can be identical or non-identical. In preferred embodiments, the organic scaffold is a calixarene or ($C_8$-$C_{12}$)aryl (FIG. 8). In most preferred embodiments, the organic scaffold is a non-cyclic calix[2]arene (FIG. 10) or a cyclic calix[4]arene (FIG. 4). It is not necessary that each calixarene unit or each available substitution position of a ($C_8$-$C_{12}$)aryl be attached to a peptide loop.

Thus, by way of example, in a preferred embodiment, growth factor binding compounds or agents are of the general structure of Formula I:

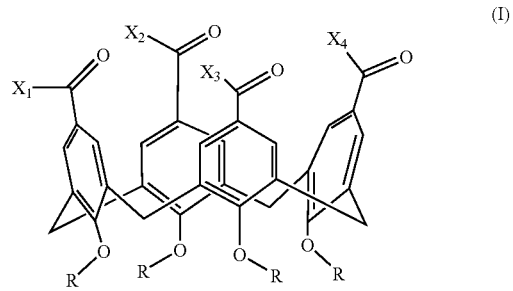

Figure 6:
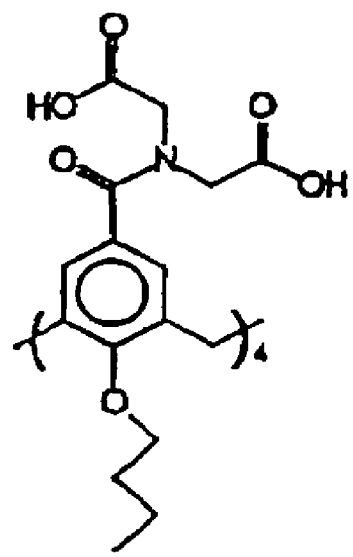
FIG. 6 illustrates the structure of calix tails.

(I)

where R is substituted or unsubstituted ($C_1$-$C_{12}$)alkyl, ($C_7$-$C_{18}$)aralkyl, ($C_6$-$C_{18}$)aryl, ($C_1$-$C_{12}$)alkenyl, ($C_7$-$C_{18}$)aralkenyl, ($C_1$-$C_{12}$)alkylether, or the like. In certain embodiments, R is n-butyl, n-propyl, benzyl, or an alkyl ether such as O-3 or O-4 as illustrated in FIG. 6. In these preferred embodiments, $X_1$, $X_2$, $X_3$, and $X_4$ comprise different or identical cyclic peptide loops of the general structure of Formula II.

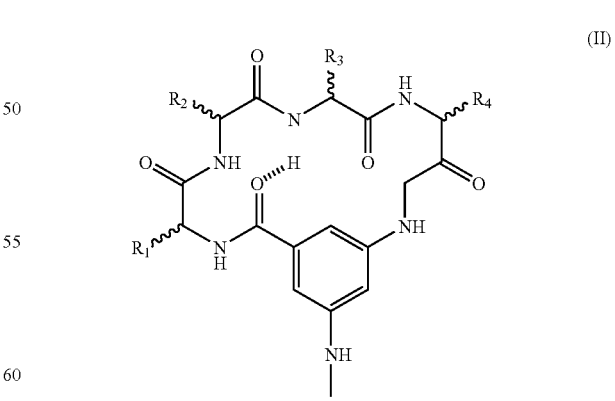

(II)

The present invention therefore relates to a family of synthetic molecules that, like the antibodies, have multiple peptide loops as the recognition site but built around a rigid organic framework. The design retains a similar structural relationship to an antigen combining region but based on four loops rather than six as occurs in natural antibodies. However, it should be noted that X-ray structures of antibody-antigen complexes show that often only four of the six available loops of natural antibodies make contact to the antigen. See, e.g., Wilson, I. A.; Stanfield, R. L.; Rini, J. M.; Arevalo, J. H.; Schulze-Gahmen, U.; Fremont, D. H.; Stura, E. A.; "Structural Aspects of Antibodies and Antibody-Antigen Complexes" Ciba Foundation Symp. 1991, 159, 13-39. Also, the synthetic route described herein allows the ready generation of large libraries of growth factor binding agents that can be screened for binding to target growth factors. The basic design of an embodiment of a growth factor binding compound of the present invention is shown in FIG. 1. A scaffold is provided by a calixarene unit containing four arylcarboxylate groups linked by ortho substitution within a macrocyclic ring. The para-alkyloxy substituent enforces an essentially rigid conformation for the calixarene with all four carboxylate groups projecting onto the same side of the ring, that is, on the same side of an imaginary plane passing through the benzyl rings. This conformation allows the close positioning of four peptide loops in direct analogy to the antigen combining site of antibodies.

The peptide loop components are prepared via the route outlined in greater detail herein. Part of the design is the dipeptide mimetic 3-aminomethylbenzoic acid which allows the formation of a well-defined loop structure corresponding to a type-II.beta.-turn (Bach, A. C.; Eyerman, C. J.; Gross, J. D.; Bower, M. J.; Harlow, R. L.; Weber, P. C.; DeGrado, W. F. "Structural Studies of a Family of High Affinity Ligands for GPIIb/IIIa," J. Am. Chem. Soc. 1994, 116, 3207-3219) but with the potential for attachment to the calixarene scaffold. This is achieved by substitution in the 5-position by a nitro group which is then converted during the synthesis to an amino group for attachment to the calixarene. The synthesis of the cyclic peptides involves either solid phase chemistry or solution phase chemistry using a Kaiser oxime carboxylate activating group, discussed in greater detail in U.S. Pat. No. 5,770,380 to Hamilton, et al., issued Jun. 23, 1998, which is hereby incorporated in its entirety by reference.

Synthesis of the growth factor binding agents is carried out for both cyclic peptide and calixarene. Final coupling involves conversion of the calixarene tetraacid to the corresponding tetraacid chloride followed by reaction with the cyclic peptide amine derivative. This strategy allows the user to easily prepare large libraries of growth factor binding agents based on cyclic peptides with different sequences of four amino acids in the loop. Thus for 8 different peptide loop structures a total of 1,044 different growth factor binding agents will be available. By increasing the number of different peptide loops in the synthesis the diversity of artificial combining site structures can increase dramatically.

The structure thus synthesized, as illustrated in FIG. 1, shows clearly the formation of a well-defined growth factor recognition site formed by the four peptide loop components. The power of this strategy is that a large number of growth factor binding agents can be prepared by the synthetic strategy and these can be screened for high affinity binding to a range of different growth factor targets. The potential applications include substitution of synthetic growth factor binding agents into much of the current antibody technology (immunosensors, diagnostic kits, etc.). The increased stability of these compounds has further application in therapeutics as well as the identification of catalysts that can function under extreme conditions.

Accordingly, a preferred method of practicing the present invention involves screening growth factor binding agents of the present invention. In accordance with this method, a library consisting of a large number of different growth factor binding agents is provided, each of the growth factor binding agents comprising a structure as described herein, preferably an organic scaffold to which is linked a plurality of peptide loops. Each growth factor binding agent in the library differs from each of the other growth factor binding agents in the library by having a different combination of peptide loops relative to the other growth factor binding agents in the library. Once the library of growth factor binding agents is provided, each of the growth factor binding agents in the library is capable of being screened for growth factor binding agent effectiveness relative to other growth factor binding agents in the library by determining a binding affinity of the particular growth factor binding agent in the library being screened with respect to a growth factor relative to a binding affinity of one or more other growth factor binding agents in the library to that same target antigen. Additionally, the library may be used by focusing on a particular growth factor binding agent and screening that growth factor binding agent for binding affinity with respect to a number of different target growth factors.

Referring again to Structure I, the scaffold comprises a calixarene ring wherein each of the arene groups that are part of the calixarene ring is linked to a peptide loop X via a linking unit, preferably a 3-aminomethylbenzamide group, such as 3-aminomethyl-5-aminobenzamide (see FIG. 1) and each of said 3-aminomethylbenzamide groups is linked to the peptide loop. Of course, other combinations, other linking groups, other organic complexes, and other peptide loop structures are possible as will now be readily apparent to those of ordinary skill in the art. Examples of other possible linking units include 3-aminophenylacetamide and 7-aminonaphthyl-1-carboxamide.

Referring now to Structure II, $R_1$, $R_2$, $R_3$, and $R_4$, represent amino acid sidechains or derivatized or analogs of amino acid sidechains. Thus, in certain embodiments, $R_{1-4}$ are sidechains of naturally occurring amino acids, such as lysine, arginine, histidine, phenylalanine, serine, alanine, leucine, tyrosine, tryptophan, glutamic acid, glutamine, aspartatic acid, asparagine, isoleucine, valine, methionine, threonine and cysteine. It will be appreciated by one of ordinary skill in the art that $R_{1-4}$ can also comprise modified or unusual amino acids sidechains, such as those disclosed in WIPO Standard ST.25 (1998), Appendix 2, Table 4A, or can comprise labeled moieties such as fluorescent labels or radiolabels. It will further be appreciated that the amino acids comprising the peptide loops can also be D-amino acids, L-amino acids, or both within a single peptide loop. In the present invention, a peptide loop rather than an open-ended peptide chain is preferred because such loops are more chemically stable than open-ended chains.

In specific embodiments of the present invention, a calixarene scaffold is used because its ring structure and non-protein nature give it stability in extreme environmental conditions and in the presence of protease enzymes. In addition, its ring structure, as detailed below, helps force the attached peptide loops to come into close proximity to each other, mimicking the binding site of an antibody. Finally, the arene groups of the calixarene rings may be attached at their number four positions to alkyloxy groups.

The above-mentioned alkyloxy groups are important in the preferred embodiment of the present invention because they enforce the rigid three-dimensional conformation of the calixarene scaffold. In two dimensions, calixarene is a ring, however, in three dimensions the ring is seen to have a cup-like conformation, as is illustrated in FIG. 1. The side of the cup from which the alkyloxy groups project, that is, the "4"

positions of the arene groups, may be called the bottom of the cup. Thus the opposite side, which is the side attached to the peptide loops, that is, the "1" positions of the arene groups, may be called the top of the cup. Because the alkyloxy groups (OR) attached to the bottom of the cup reenforce the cup conformation, all of the peptide loops X at the top of the cup are forced into close proximity to one another. This close proximity of the peptide loops, in turn, mimics the structure of an antibody and forces all of the peptide loops to be available for contact with and binding to an antigen of interest.

In formula II, $R_1$, $R_2$, $R_3$, and $R_4$, are each amino acid side chains that define a tetra-peptide sequence in which the tetra-peptide is covalently attached at the amino and carboxy termini of the tetra-peptide to a 3-aminomethyl-5-aminobenzamide linking group. In certain embodiments, for example PDGF-binding embodiments, the tetra-peptide sequence is selected from the group consisting of GDFD (SEQ ID NO. 1), GDDD (SEQ ID NO. 2), D-ADGD (SEQ ID NO. 3) in which the alanine is in the D conformation, other amino acids being in the L conformation), GDLD (SEQ ID NO. 4), GDAD (SEQ ID NO. 5), GDGY (SEQ ID NO. 6), ADGD (SEQ ID NO. 7), GDSD (SEQ ID NO. 8), GKGF (SEQ ID NO. 9), GKGK (SEQ ID NO. 10), GDND (SEQ ID NO. 11), PDGD (SEQ ID NO. 12), GDDG (SEQ ID NO. 13), GDDY (SEQ ID NO. 14), and functionally related derivatives thereof. In this embodiment, the preferred R group is n-butyl.

In an alternative embodiment, the growth factor binding compound has the structure of Formula III:

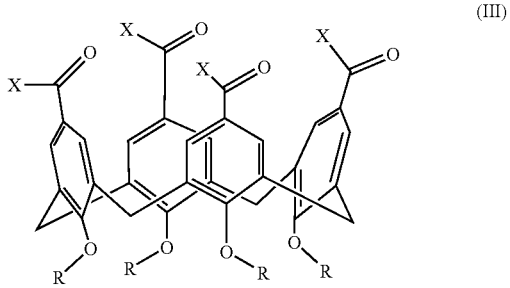

(III)

Here, X comprises attached identical cyclic peptide loops as illustrated by structure II, wherein $R_1$, $R_2$, $R_3$ and $R_4$, are each amino acid side chains that define the tetrapeptide sequence, in which the tetrapeptide is covalently attached at the amino and carboxy termini of the tetrapeptide to a 3-aminomethyl-5-aminobenzamide.

Figure 9:
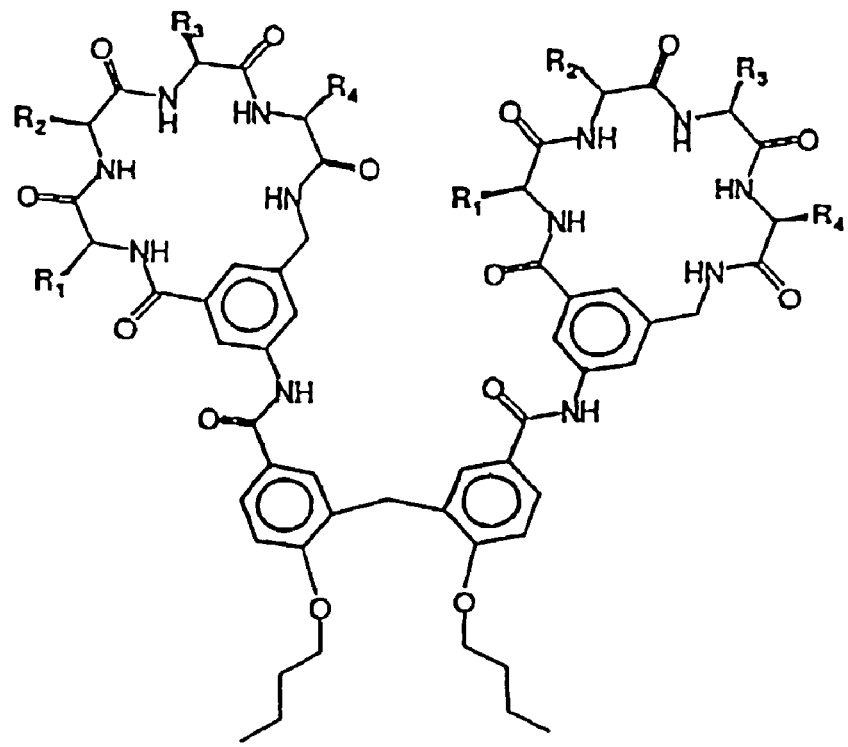
FIG. 9 illustrates the structures of GFB-126 and GFB-127.

It will be apparent to those of ordinary skill that not every substitutable position of the organic scaffold need be attached to a peptide loop. Thus, embodiments having a calix[4] arene organic scaffold with fewer than 4 peptide loops attached to it are envisaged as within the scope of the present invention (see, for example, FIG. 9). It will further be appreciated that numerous permutations of both the positioning of specific peptide loops, and the corresponding unsubstituted positions within the organic scaffold, are possible within the present invention.

A pharmaceutical composition is formed by means such as known by those skilled in the art, wherein, for example, the compound of Formula I, or Formula III, or a salt thereof, or a combination thereof, is incorporated into a pharmaceutically acceptable carrier. These pharmaceutical compositions can be used for treatment of a subject who suffers from excess cellular proliferation, including restenosis, excess angiogenesis, a tumor, a condition comprising undesirable angiogenesis, or a combination thereof. Applications in both veterinary and human use are indicated.

Where a subject has one or more tumors, treatment can comprise administering to the subject an effective amount of a composition comprising, for example, Formula I or Formula III or their respective salts, and a pharmaceutically acceptable carrier. The compositions are suitable for the treatment of all tumors requiring activation by growth factors or angiogenesis for tumor growth, such as glioblastomas, adenosarcomas, and sarcomas. Further examples of tumors treatable through the present invention, include, but are not limited to:

paranasal sinus, nasopharynx, oral cavity and oropharynx squamous cell carcinomas and adenocarcinomas; oral lymphomas; adenoid cystic carcinoma; paragangliomas; squamous cell carcinoma, adenocarcinoma, large cell (undifferentiated) carcinoma, and small cell carcinoma of the lung; mediastinal thymomas, lymphomas and neurogenic carcinomas; squamous cell carcinoma and adenocarcinoma of the esophagus; adenocarcinoma of the stomach; ductal adenocarcinoma, mucinous cystadenocarcinoma, acinar cell carcinoma, unclassified large cell carcinoma, small cell carcinoma, and pancreatoblastoma of the pancreas; hepatocellular carcinoma, hepatoblastoma, cholangiocarcinoma, cholangiocellular carcinoma, cystadenocarcinoma, squamous cell carcinoma, angiosarcoma, hemangioendothelioma, leiomyosarcoma, malignant schwannoma, fibrosarcoma, malignant fibrous histiocytoma, lymphoma, osteosarcoma, rhabdomyosarcoma and mesenchymal sarcoma of the liver; adenosarcoma, squamous cell carcinoma, adenosquamous carcinoma, oat cell carcinoma (small cell), carcinosarcoma, malignant lymphoma, malignant melanoma, rhabdomyosarcoma, fibrous histiocytoma, and angiosarcoma of the gallbladder; adenocarcinoma, fibrosarcoma, leiomyosarcoma, liposarcoma, angiosarcoma, lymphangiosarcoma, lymphoma, and neurofibrosarcoma of the small bowel; adenocarcinoma, mucinous adenocarcinoma, signet-ring cell adenocarcinoma, squamous cell carcinoma, adenosquamous carcinoma, undifferentiated carcinoma, unclassified carcinoma, argentaffin carcinoid tumor, nonargentaffin carcinoid tumor, composite carcinoid tumor, and leiomyosarcoma of the large intestine; squamous cell carcinoma, transitional (cloacogenic) carcinoma, adenocarcinoma, papillary villous carcinoma, and mucinous adenocarcinoma of the anus; renal clear cell, granular cell and sarcomatoid carcinoma; nephroblastoma; transitional cell carcinoma of the ureter; carcinoma of the bladder; adenocarcinoma of the prostate; squamous cell carcinoma and adenocarcinoma of the cervix; adenocarcinoma, cystadenocarcinoma, carcinoma, and adenofibroma, cystadenofibroma, sarcoma, and adenoacanthoma of the ovary; papillary, follicular, and medullary carcinoma of the thyroid; adenoma and carcinoma of the parathyroid; adenoma and carcinoma of the adrenal cortex; fibrosarcoma, and fibrous histiocytoma, liposarcoma, squamous cell carcinoma, and sarcoma of soft tissues; leiomyosarcoma, and rhabdomyosarcoma of muscle tissues; osteogenic sarcoma, fibrosarcoma, fibrous histiocytoma and chondrosarcoma of bone; angiosarcoma, lymphangiosarcoma, and Kaposi's sarcoma; malignant glomus tumor and hemangiopericytoma; synovial sarcoma and giant cell tumor of the tendon sheath; malignant peripheral nerve sheath tumor, neurofibrosarcoma, malignant triton tumor, malignant glandular schwannoma, epithelioid schwannoma, malignant granular cell tumor, nerve clear cell sarcoma, and malignant paraganglioma; chondrosarcoma and osteosarcoma; and malignant mesencymoma.

The compositions are effective over a wide range of concentrations. The effective amounts are those suitable to bring the concentration in the biological fluid of the subject to between about 1 picomolar and about 1 millimolar, preferably between about 10 nanomolar and about 10 micromolar, most preferably about 0.2 micromolar. Alternatively, the effective amount can be expressed in terms of the body weight of the subject. An amount effective to treat the disease is between about 0.3 micrograms per kilogram of body weight to about 330 miligrams per kilogram of body weight. Most preferably a concentration of about 1.0 milligrams per kilogram is suitable.

Some tumors express elevated amounts of platelet derived growth factor and/or platelet derived growth factor receptor. To measure the amount of a platelet derived growth factor in a sample, the growth factor binding compound can be radiolabeled, fluorescently labeled, labeled with a reporter enzyme, or some combination thereof. In addition, the growth factor binding compound can covalently or noncovalently attach to a surface or a particle. The covalent linkage can be through an amine linkage, an amide linkage, an ester linkage, or an ether linkage. The surface or particle can comprise of polystyrene, polyvinyl chloride, glass, ceramic, iron, or any other suitable material.

A method of delayed release of a growth factor is, for example, to administer to the patient a stoichiometric complex of the growth factor bound to its growth factor binding agent. The rate of release of growth factor is then determined by the unbinding rate constant for the complex. The growth factor of the complex can comprise variant forms of growth factor, such as, for example, xenogenic forms of platelet derived growth factor, or chemically derivatized versions of platelet derived growth factor.

9. EXAMPLES

The following specific examples are provided to better assist the reader in the various aspects of practicing the present invention. As these specific examples are merely illustrative, nothing in the following descriptions should be construed as limiting the invention in any way. Such limitations are, of course, defined solely by the accompanying claims.

9.1 Materials and Methods

Inhibition of PDGF-dependent Receptor Tyrosine Phosphorylation by Growth Factor Binding Agents.

Starved NIH 3T3 cells are pretreated with various growth factor binding agents (0-100 μM) for 5 min before stimulation with PDGF (10 ng/mL) for 10 min. The cells are then harvested and lysed, and the proteins from the lysates separated by SDS-PAGE and immunoblotted with an anti-phosphotyrosine antibody (4G10: Upstate Biotechnology, Lake Placid, N.Y.). The phosphotyrosine PDGF receptor bands are scanned, and the concentrations of growth factor binding molecules that inhibited the ability of PDGF to stimulate PDGFR tyrosine phosphorylation by 50% are determined.

PDGF Binding

GFB-111 (50 μM) is incubated with buffer A (PBS 0.5% BSA) or PDGF-BB (1, 3 and 4.mu.M in buffer A) at room temperature for 10 minutes. The mixtures are then loaded onto a native 4% PAGE. The gel is then stained with silver nitrate. Duplicate lanes are run in the same gel but are not stained. Bands corresponding to the boxed area are cut out of the lanes of the gel that is not stained, denatured with SDS-PAGE loading buffer (Tris 100 mM pH 6.8, 15% Glycerol, 3% SDS, 7.5% b-mercaptoethanol, 0.05% bromophenol blue), loaded onto a 4% SDS-PAGE gel and silver stained.

Binding of [$^{125}$I]-PDGF to NIH 3T3 Cells: Inhibition by GFBs.

NIH 3T3 (PDGF) or NIH 3T3 cells overexpressing either EGFR (EGF), IGFR (IGF) or Flk-1 (VEGF), are incubated with [$^{125}$I]-PDGF, [$^{125}$I]-EGF, [$^{125}$I]-IGF or [$^{125}$I]-VEGF, respectively (50,000 cpm per well) and increasing concentrations of GFB-111 or GFB-116. Cells are incubated at 4° C. for 1-3 h. After discarding media, the cells are washed 3 times with PBS and three times with Tris 25 mM pH 8.0, 1% T-X-100, 10% glycerol, 1% SDS. Lysates plus wash are counted. Excess of cold growth factors is used to obtain non-specific binding levels.

PDGF-stimulated Receptor Tyrosine Autophosphorylation and Activation of MAPK.

Starved NIH 3T3 cells (PDGF-BB and PDGF-AA), NIH 3T3 cells overexpressing either EGFR (EGF) or Flk-1 (VEGF) are pre-treated with the indicated concentrations of GFB-111 for 5 minutes before 10 minutes of stimulation with PDGF-BB (10 ng/ml), PDGF-AA (10 ng/ml), EGF (100 ng/ml) and VEGF (50 ng/ml). Cell lysates are run on SDS-PAGE gels, then transferred to nitrocellulose and Western blotted with anti-phosphotyrosine (4G 10) or anti-phosphorylated Erk1/Erk2 (New England Biolabs).

In other experiments, starved NIH 3T3 cells (PDGF-AA, PDGF-BB, aFGF, bFGF), NIH 3T3 cells overexpressing EGFR, IGF-R or Flk-1 and the human breast carcinoma SkBr3 that overexpresses ErbB2 (HRGβ) are pretreated with GFB-111 (100 μM) for 5 min before 10 min stimulation with the indicated growth factors at the concentrations shown above and aFGF (10 ng/ml), bFGF (50 ng/ml), IGF-1 (50 ng/ml) and HRGβ (10 ng/ml). Cell lysates are then immunoblotted with anti-phospho Erk1/Erk2 as described above.

PDGF-stimulated DNA Synthesis.

Starved NIH 3T3 or NIH 3T3 overexpressing IGFR are treated for 16 hours with indicated concentrations of GFB-111 and either 10 ng/ml PDGF or 50 ng/ml IGF-1, respectively, then labeled for 2 hr (NIH 3T3) or 4 hr (IGFR) with $^3$H-thymidine. Cells are then washed in PBS, lysed in 0.1N NaOH and spotted onto glass fiber filters. DNA is precipitated with ice cold ethanol then $^3$H-thymidine incorporation quantified by scintillation counting.

Antitumor Efficacy Studies in Nude Mice.

U87MG cells (human glioblastoma) are harvested, resuspended in PBS and injected s.c. into the right and left flank (10×10$^6$ cells per flank) of 8 week old female nude mice (Charles River, Wilmington, Mass.). When tumors reached about 100 mm$^3$, animals are dosed i.p. with 0.2 ml once daily. Control animals received a saline vehicle whereas treated animals are injected with GFB-111 (50, 100 or 200 mg/kg/day). The tumor volumes are determined by measuring the length (l) and the width (w) and calculating the volume (V=lw$^2$/2) as described previously. For detection of phosphorylated/activated Erk1/Erk2 in tumors in vivo, the tumors are extracted 20 min after the last GFB-111 injection on day 32, rinsed and the tissue homogenized in HEPES lysis buffer (30 mM Hepes, pH 7.5, 1% T-X-100, 10% glycerol, 10 mM NaCl, 5 mM MgCl$_2$, 25 mM NaF, 1 mM EGTA, 2 mM Na$_3$VO$_4$, 10 μg/ml trypsin inhibitor, 25 μg/ml leupeptin, 10 μg/ml aprotinin, 2 mM PMSF). The lysates (50-100 μg) are electrophoresed on a 15% SDS-PAGE, transferred to nitrocellulose membranes and immunoblotted, with anti-phospho-p44/p42 MAPK (Thy202/Tyr204).

Angiogenesis Studies.

On the indicated termination day of each nude mouse experiment described above, (see also Table 2), the tumors are extracted and half frozen at −70° C., and half is fixed in 10% neutral buffered formalin for 6 hrs. After fixation the tissue samples are processed into paraffin blocks. Four micrometer-thick tissue sections are obtained from the paraffin blocks and stained with hematoxylin and eosin (H&E) (Richard-Allan Scientific, Kalamazoo, Mich.) using standard histologic techniques. Tissue sections are also subjected to immunostaining for Factor VIII using the avidin biotin peroxidase complex technique (Vectastatin Elite ABC Kit, Vector, Burlingame, Calif.). Rabbit polyclonal FVIII antibody (Von Willebrand Factor, Dako Corporation, Carpinteria, Calif.) is used at 1:400 dilution, following microwave antigen retrieval (4 cycles of 5 minutes each on high in 0.1M citrate buffer).

Example 1

PDGF Binding Agents 9.2 Design of Molecules that Bind PDGF and Disrupt its Signaling Function A novel series of protein surface binding agents are prepared that bind PDGF and disrupt its signaling function. The molecules are composed of a central calix[4]arene scaffold to which is attached four peptide loop domains (FIG. 1). The peptide loop component is based on a cyclic hexapeptide in which two residues are replaced by a 3-aminomethylbenzoate dipeptide mimetic containing a 5-amino substituent for attachment to the scaffold. The resulting molecules (as shown in Table 1) contain a functionalized and variable surface approximately 500 Å$^2$ in area. Several peptide loop sequences are synthesized (Table 1) to provide molecular surfaces with negatively and positively charged as well as hydrophobic regions designed to bind to complementary areas on the target growth factor. To identify PDGF binding molecules from this library, a cell-based screening assay is developed with NIH 3T3 cells to detect molecules capable of blocking PDGF-BB-induced tyrosine autophosphorylation of the PDGF receptor. The ability of the identified molecules to bind PDGF-BB and inhibit interaction with its receptor is then confirmed biochemically. Starved NIH 3T3 cells are pretreated for 5 min with the synthetic molecules prior to stimulation with PDGF for 10 min. The effects of the molecules on PDGF-stimulated receptor tyrosine phosphorylation are determined by the antiphosphotyrosine Western blotting as described in Table 1. GFB-111 is identified as one potential PDGF binder and as a potent ($IC_{50}$=250 nM) inhibitor of PDGF-BB-stimulation of PDGF receptor tyrosine autophosphorylation (Table 1). GFB-111 has four-fold symmetry containing 4 identical peptide loops with negative and hydrophobic residues, GlyAspGlyTyr (GDGY) (SEQ ID NO. 6), that are designed to be complementary to the PDGF surface involved in binding to PDGFR. The area of PDGF-BB that binds PDGFR is composed primarily of positive and hydrophobic residues. Substitution of aspartic acid in the loop by positively charged lysine is poorly tolerated as can be seen by comparison of GFB-111 (GDGY) (SEQ ID NO. 6) ($IC_{50}$=250 nM) to GFB-115 (GKGF) (SEQ ID NO. 9) ($IC_{50}$=50 μM) and GFB-116 (GKGK) (SEQ ID NO. 10) ($IC_{50}$=40 μM), indicating that negatively charged residues are important for the inhibitory activity of GFB-111. However, negatively charged residues along are not sufficient and the presence of an aromatic hydrophobic residue in the loop increases affinity as can be seen by comparison of GFB-111 (GDGY) (SEQ ID NO. 6) with GFB-107 (GDGD) (SEQ ID NO. 16) ($IC_{50}$=2.5 μM) as well as of GFB-122 (GDDY) (SEQ ID NO. 14) ($IC_{50}$=1.7 μM) with GFB-106 (GDDD) (SEQ ID NO. 2) ($IC_{50}$=8 μM) (Table 1).

TABLE 1

Inhibition of PDGF stimulated PDGFR Tyrosine Phosphorylation and Signaling in NIH 3T3 by GFBs

| | | | ($IC_{50}$) Inhibition (μM) | |
|---|---|---|---|---|
| Designation | Scaffold | $R_1$-$R_4$ sequence | PDGFR-Y-P | p42/Erk2 |
| GFB-101 | O4-Calix[4] | 4-GFGD (SEQ ID NO. 15) | >500 | >500 |
| GFB-102 | " | 4-GDFD (SEQ ID NO. 1) | >500 | 500 |
| GFB-103 | " | 4-GDGD (SEQ ID NO. 16) | >500 | >500 |
| GFB-104 | O3-Calix[4] | 4-GDGD (SEQ ID NO. 16) | >500 | >500 |
| GFB-105 | But-Calix[4] | 4-GDFD (SEQ ID NO. 1) | 2.4 | 28 |
| GFB-106 | " | 4-GDDD (SEQ ID NO. 2) | 8 | 33 |
| GFB-107 | " | 4-GDGD (SEQ ID NO. 16) | 2.5 | 10 |
| GFB-108 | " | 4-d-ADGD[1] (SEQ ID NO. 3) | 9 | 57 |
| GFB-109 | " | 4-GDLD (SEQ ID NO. 4) | 7.5 | 15 |
| GFB-110 | " | 4-GDAD (SEQ ID NO. 5) | 1.7 | 7 |
| GFB-111 | " | 4-GDGY (SEQ ID NO. 6) | 0.25 | 2.6 |
| GFB-112 | " | 4-ADGD (SEQ ID NO. 7) | 29 | 26 |
| GFB-113 | " | 4-GDSD (SEQ ID NO. 8) | 2.8 | 30 |
| GFB-114 | " | (4-) 8-acid (See FIG. 7) | >50 | >50 |
| GFB-115 | | 4-GKGF (SEQ ID NO. 9) | >50 | >50 |
| GFB-116 | | 4-GKGK (SEQ ID NO. 10) | 40 | 28 |
| GFB-117 | | 4-GDND (SEQ ID NO. 11) | 5.8 | 36 |
| GFB-118 | | 4-D-2-NalDGD[2] (SEQ ID NO. 17) | 0.7 | 1.2 |
| GFB-119 | | 4-PDGD (SEQ ID NO. 12) | 20 | 32 |
| GFB-120 | " | 4-GDDG (SEQ ID NO. 13) | 1.3 | 1.7 |
| GFB-121 | " | 4-D-AbuDGD[3] (SEQ ID NO. 18) | 5.6 | 8.5 |
| GFB-122 | " | 4-GDDY (SEQ ID NO. 14) | 1.7 | 19 |
| GFB-123 | " | 1-GDDG (SEQ ID NO. 13) | >50 | >50 |
| GFB-124 | " | See FIG. 8 | >50 | >50 |

TABLE 1-continued Inhibition of PDGF stimulated PDGFR Tyrosine Phosphorylation and Signaling in NIH 3T3 by GFBs

| | | | | |
|---|---|---|---|---|
| GFB-126 | " | 3 × GDDG (See FIG. 9) (SEQ ID NO. 13) | 1.9 | 4.6 |
| GFB-127 | " | 2 × GDDG (See FIG. 9) (SEQ ID NO. 13) | 32 | >50 |
| GFB-128 | " | DPM-2-GDGY (See FIG. 10) (SEQ ID NO. 6) | 26 | >50 |
| GFB-129 | " | DPM-2-GDDD (See FIG. 10) (SEQ ID NO. 2) | | |
| GFB-130 | " | DPM-2-GDDY (See FIG. 10) (SEQ ID NO. 14) | | |
| GFB-131 | " | DPM-2-GDDG (See FIG. 10) (SEQ ID NO. 13) | | |

Figure 11:
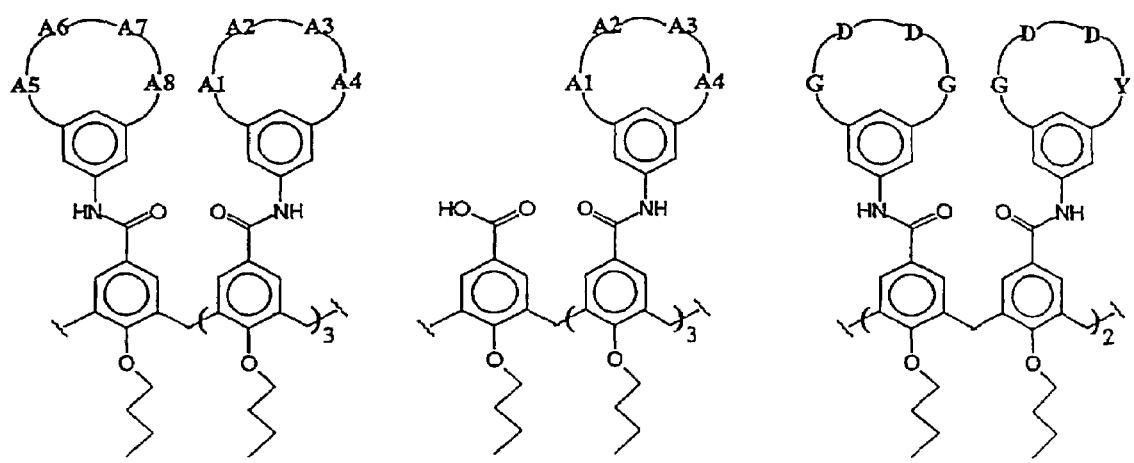
FIG. 11 illustrates the structures of GFB-132 through GFB-137.

| | | | ($IC_{50}$) Inhibition (μM) | | |
|---|---|---|---|---|---|
| | | | | p42/Erk2 | |
| Designation | Scaffold | $R_1$-$R_4$ sequence | PDGFR-Y-P | p42 | p44 |
| GFB-132 | But-Calix | 3-GDGY (SEQ ID NO. 6)-1-GDDG (SEQ ID NO. 13) (See FIG. 11) | 0.4 | 2.9 | 3 |
| GFB-133 | " | 3-GDGY (SEQ ID NO. 6)-1-$CO_2$H (See FIG. 11) | 0.8 | 3.2 | 3 |
| GFB-134 | " | 3-GDGY (SEQ ID NO. 6)-1-GDDY (SEQ ID NO. 14) (See FIG. 11) | 1.9 | 2.5 | 2.6 |
| GFB-135 | " | 3-GDGY (SEQ ID NO. 6)-1-GDDD (SEQ ID NO. 2) (See FIG. 11) | 1.9 | 3.2 | 24 |
| GFB-136 | " | 3-GDDD (SEQ ID NO. 2)-1-GDGY (SEQ ID NO. 6) (See FIG. 11) | 3 | 25 | 24 |
| GFB-137 | " | 2-GDGY (SEQ ID NO. 6)-1-GDDG (SEQ ID NO. 13) (See FIG. 11) | 0.4 | 2.9 | 47 |

[A]The difference between GFB-101 through GFB-103 (O4-Calix), GFB-104 (O3-Calix), and the rest of the GFB compounds (But-Calix) is related to the structure of the calix tail. (Please refer to FIG. 6.)
[1]GFB-108: The "d" refers to D-amino acid, so-ADGD is (D-Ala)-Asp-Gly-Asp (SEQ ID NO. 3).
[2]GFB-118: D-2 Nal is structurally related to D-Phe. Instead of the phenyl ring in Phe, it has a naphthelene ring linked through the 2-position.
[3]GFB-121: d-Abu is D-aminobutyric acid. It has an ethyl group in the side chain while Ala has a methyl group in the side chain.

Starved NIH 3T3 cells are pretreated with the various GFBs (0-100 μM) for 5 min. prior to stimulation with PDGF (10 ng/ml) for 10 min. The cells are then harvested lysed and the proteins from the lysates are separated by SDS-PAGE and immunoblotted with an anti-phosphotyrosine antibody (4G10, Upstate Biotechnology, Lake Placid, N.Y.). The phosphotyrosine PDGF receptor bands are scanned and the concentrations of GFBs that inhibit the ability of PDGF to stimulate PDGFR tyrosine phosphorylation by 50% are determined. Data for each compound is representative of at least two independent experiments. FIG. 1 illustrates the structure of growth factor binders. GFBs are synthesized as described by Park, H. D. et al., Protein surface recognition by synthetic receptors: A route to novel sub-micromolar inhibitors for chymotrypsin. *J. Am. Chem. Soc.* 121, 8-13 (1999); and Hamuro, Y. et al., A calixarene with four peptide loops: An antibody mimic for recognition of protein surfaces. *Angew. Chemie Int. Ed. Engl.* 36, 2680-2683 (1997), each herein incorporated by reference in its respective entirety.

9.3 GFB-111 is a PDGF-BB Binding Molecule

The structure activity relationship results in Table 1 are consistent with GFB-111 being a PDGF-BB binding molecule. Whether GFB-111 binds PDGF-BB and also inhibits binding of [$^{125}$I] PDGF to its receptor on NIH 3T3 cells is determined by gel electrophoresis by mixing GFB-111 with PDGF-BB. This results in a concentration-dependent disappearance of GFB-111 which is paralleled by the appearance of a slower migrating band on native polyacrylamide gel electrophoresis (PAGE). In this native PAGE system, PDGF-BB itself migrates toward the cathode and hence does not penetrate the gel. To demonstrate that the slower migrating band is formed by the complex between GFB-111 and PDGF-BB, the band is cut out of the native gel, processed and loaded onto denaturing SDS-PAGE gel. FIG. 2B illustrates that the GFB-111 standard (lane 5) as well as the GFB-111 band cut out of FIG. 2A gel (lane 1) migrates on SDS-PAGE as a single band that elutes faster than the dye front. Their separation on SDS-PAGE (lane 2) is confirmed by mixing PDGF-BB standard (lane 4) and GFB-111 standard (lane 5). Note that the band cut out of the native gel presumed to contain the complex does indeed contain both PDGF-BB and GFB-111 (FIG. 2B, lane 3). The interaction is structure-dependent since the positively charged derivative GFB-116 (Table 1) does not bind to PDGF-BB as demonstrated by gel electrophoresis. Furthermore, GFB-111 does not bind to the related peptide growth factors EGF (epidermal growth factor) and IGF-1 (insulin-like growth factor-1) demonstrating that GFB-111 is selective for PDGF.

GFB-111 is incubated with increasing concentrations of PDGF-BB and the mixtures are then loaded onto native PAGE. Bands corresponding to the boxed area are cut out of the lanes of the gel, denatured with SDS-PAGE loading buffer, loaded onto a 4% SDS-PAGE gel and silver stained as described under Methods. Lanes 1-6 correspond to GFB-111 from the native gel; PDGF+GFB-111 standards; GFB-111/PDGF complex from the native gel; PDGF standard; GFB-111 standard and buffer, respectively. Data are representative of three independent experiments.

9.4 Complementarity of the Recognition Domain of GFB-111 with the Receptor Binding Surface of All PGDF The complementarity of the recognition domain of GFB-111 (negatively charged and hydrophobic residues) with the receptor binding surface of PDGF (positively charged and hydrophobic sites) suggests that GFB-111 blocks binding of PDGF to PDGFR. Whether GFB 111 can block [$^{125}$I]-PDGF-BB specific binding in NIH 3T3 cells is determined by pretreatment of the PDGF-BB with increasing concentrations of GFB-111. FIG. 2C illustrates that in the absence of GFB-111, [I]-PDGF-BB is bound by NIH3T3 cells. However, pre-treatment with increasing concentrations of GFB-111, results in a concentration-dependent decrease in PDGF-BB binding. The $IC_{50}$ value of binding inhibition is 250 nM (FIG. 2C) which is similar to the $IC_{50}$ value of GFB-111 inhibition of PDGF-BB-stimulated PDGFR tyrosine phosphorylation (Table 1). FIG. 2C also shows that PDGF-BB binding to its receptor is blocked by GFB-111 but not by GFB-116. Similar experiments with EGF, IGF-1 and VEGF (vascular endothelial growth factor) demonstrate a lack of significant effects of GFB-111 (10 µM) on [$^{125}$I]-EGF or [$^{125}$I], [$^{125}$I]-IGF-1 binding but inhibition of [$^{125}$I]-VEGF binding by 50% in NIH 3T3 cells overexpressing EGFR, IGF-1R and VEGFR (Flk-1), respectively (FIG. 2D).

9.5 Selectivity of GFB-111

The selectivity of GFB-111 is shown by its ability to block growth factor-stimulated tyrosine phosphorylation of several receptor tyrosine kinases and subsequent activation of two mitogen-activated protein kinases (MAPK), Erk1 and Erk2. FIG. 3A shows that PDGF-BB-stimulation of starved NIH 3T3 cells in the absence of GFB-111 results in PDGFR autophosphorylation and Erk1/Erk2 activation. However, pretreatment of these cells with GFB-111 (0.1 to 10 µM) for 5 min results in a concentration-dependent inhibition of PDGF-BB stimulation of receptor tyrosine phosphorylation with an $IC_{50}$ of 250 nM and a complete block at 3 µM GFB-111. FIG. 3A also shows that GFB-111 is a potent inhibitor of PDGF-dependent activation of Erk1 and Erk2 ($IC_{50}$ of 0.8 and 1.2 µM, respectively). PDGF-AA stimulation of PDGF receptor phosphorylation and Erk1/Erk2 activation is also blocked with GFB-111 with a similar potency. In contrast, GFB-111 at concentrations as high as 100 µM does not affect the ability of EGF to stimulate EGFR tyrosine phosphorylation and Erk1/Erk2 activation. For comparison, PD158780, a known EGFR tyrosine kinase inhibitor, blocks EGFR tyrosine phosphorylation and Erk1/Erk2 activation (FIG. 3A). GFB-111 is able to inhibit VEGF-stimulated Flk-1 tyrosine phosphorylation and MAPK activation but at concentrations higher ($IC_{50}$=10 µM) than those required for PDGF ($IC_{50}$=250 nM). Furthermore, IGF-1-, aFGF-, bFGF- and HRGβ-activation of Erk1/Erk2 is minimally affected by GFB-111 at concentrations as high as 100 µM (FIG. 3B). Thus, GFB-111 blocks PDGF signaling at very low concentrations, inhibits VEGF signaling at higher concentrations (10 µM), but has negligible effect on EGF, IGF-1, aFGF, bFGF and HRGβ signaling at very high concentrations.

9.6 The Effectiveness of GFB-111 on PDGF-Induced Cellular Responses.

The selectivity of PDGF-induced cellular responses, is evaluated by the selectivity of GFB-111 to inhibit growth factor-stimulated DNA synthesis using a [$^3$H]-thymidine incorporation assay. In NIH 3T3 cells PDGF-BB stimulated DNA synthesis by 10-fold and GFB-111 suppresses this stimulation in a dose dependent manner with an $IC_{50}$ of 6.5 µM (FIG. 4). In contrast GFB-111 is ineffective at inhibiting IGF-1-stimulated DNA synthesis at concentrations as high as 100 µM (FIG. 4). These data further confirm the highly selective character of GFB-111 towards PDGF.

9.7 The Effect of GFB-111 on Angiogenesis and Human Cancer Cell Growth in Animal Models.

The ability of GFB-111 to potently and selectively block PDGF-dependent signaling and DNA synthesis, coupled with the ability of PDGF to stimulate angiogenesis and contribute to cancer cell growth, permits determination of in vivo antitumor efficacy of GFB-111 in the nude mouse human xenograft model. FIG. 5A illustrates that daily treatment (i.p.) of nude mice implanted s.c. with the human glioblastoma U87MG with GFB-111 at 50, 100 and 200 mg per kg results on day 32 in a dose-dependent inhibition of tumor growth of 56, 81 and 88%, respectively Table 2). FIG. 5a insert illustrates that extraction and processing of tumors on day 32, shows that Erk1/Erk2 activation is blocked in the tumors from the animals treated with 100 and 200 mg per kg GFB-111. The ability of GFB-111 to inhibit tumor growth is not limited to U87MG. GFB-111 is also effective at inhibiting the tumor growth in nude mice of the human lung adenocarcinoma A-549 and the rat glioma C6 (Table 2). However, the growth of the human medulloblastoma DaOY is minimally affected at 50 mg per kg per day GFB-111 (Table 2).

TABLE 2

GFB-111 Antitumor Efficacy

| Cell line | Tumor origin | % Tumor growth inhibition Experiments | | | |
|---|---|---|---|---|---|
| | | 1 | 2 | 3 | 4 |
| U87-MG | Human brain | 61% (35) (50 mpk) | 56% (32) (50 mpk) | 81% (32) (100 mpk) | 88% (32) (200 mpk) |
| A-549 | Human lung | 62% (30) (50 mpk) | 53% (31) (50 mpk) | 64% (27) (50 mpk) | N/D |
| C6 | Rat brain | 54% (15) (50 mpk) | 64% (15) (50 mpk) | 46% (18) (50 mpk) | N/D |
| DaOY | Human brain | 21% (48) (50 mpk) | 0% (37) (50 mpk) | N/D | N/D |

9.8 Inhibition of Angiogenesis in vivo by GFB-111.

Because GFB-111 is effective at inhibiting the tumor growth of human cancer cells that express a PDGF/PDGFR autocrine loop (U87MG) as well as those that express neither PDGF nor PDGFR (A-549), and because PDGF promotes angiogenesis, the effect of GFB-111 on inhibition angiogenesis in vivo is shown. U87MG tumor biopsy specimens on day 32 are fixed and processed into paraffin blocks. Tissue sections are subjected to immunostaining with the vascular marker Factor VIII. Tumors from control animals show very marked staining. In contrast as illustrated in FIG. 5B, the Factor VIII immunostaining is decreased in a dose-dependent manner in tumors from animals treated with 50, 100 and 200 mg per kg GFB-111. Quantification of microvessels at two field magnifications (250× and 400×) clearly demonstrates that GFB-111 inhibits angiogenesis strongly in U87MG and A-549 tumors, to a lesser degree in C6 tumors, and has no effect on angiogenesis in DaOY tumors (Table 3).

TABLE 3

GFB-111 Anti-angiogenic activity

| Tumor | Group | Microvessel count (Mean ± SD) | |
|---|---|---|---|
| | | 250X | 400X |
| A-549 | Control | 15.66 ± 7.00 | 7.74 ± 2.88 |
| | GFB-111 (50 mpk) | 3.63 ± 1.36 | 2.34 ± 1.01 |
| U87-MG | Control | 66.40 ± 1.36 | 31.53 ± 7.58 |
| | GFB-111 (50 mpk) | 23.13 ± 15.69 | 12.33 ± 8.37 |
| U87-MG | Control | 23.48 ± 6.21 | 15.68 ± 3.25 |
| " | GFB-111 (50 mpk) | 10.50 ± 2.12 | 6.00 ± 1.13 |
| " | GFB-111 (100 mpk) | 7.73 ± 2.61 | 5.20 ± 1.71 |
| " | GFB-111 (200 mpk) | 5.13 ± 3.10 | 3.07 ± 1.94 |
| C6 | Control | 20.23 ± 7.84 | 9.77 ± 3.13 |
| | GFB-111 (50 mpk) | 14.27 ± 4.79 | 7.97 ± 2.83 |
| DaOY | Control | 8.07 ± 1.47 | 4.73 ± 0.90 |
| | GFB-111 (50 mpk) | 7.20 ± 2.52 | 4.80 ± 1.37 |

9.9 Sprague Dawley Rat Study:

Vascular Injury Model

Sprague Dawley rats weighing 350 to 400 g are anesthetized using intraperitoneal pentobarbital (45 mg/kg). The left common, internal and external carotid arteries may be exposed via a cervical collar incision. The left common carotid artery may be injured by the intraluminal passage of a 2F Fogarty catheter (Baxter Healthcare Corp. Santa Ana, Calif.) which is introduced via the external carotid artery inflated to 5 atm for 5 minutes. The external carotid artery may be ligated after removal of the catheter and the wound closed. Animals may be treated and cared for as recommended by the NIH Guide for the Care and Use of Laboratory Animals and the Animal Welfare Act.

Delivery of GFBs

At the time of carotid angioplasty, the contralateral jugular vein may be exposed and cannulated using PE 60 polyethylene tubing (Becton Dickinson, Sparks, Md.). The catheter is tunneled subcutaneously to the back where it is attached to an Alzet miniosmotic pump (Alza Corporation, Palo Alto, Calif.). Pumps may be precalibrated to deliver either GFBs (12.5 to 100 mg/kg/day) or DMSO for 7 days after the balloon angioplasty procedure.

Morphometric Analysis

Carotid arteries may be excised 14 days after injury and immediately fixed in 2% paraformaldehyde and dehydrated in 30% sucrose. Vessels may be then embedded in OCT medium. The arteries may be then cross-sectioned into 5 μm sections taken from the center portion of the common carotid artery and stained using Mayer's hematoxalin and eosin stain. Intimal Thicknesses may be determined by measuring the distance from the luminal surface to the internal elastic lamina. Medial thicknesses may be determined by calculating the distance from the internal elastic lamina to the external elastic lamina. The intimal and medial layer thicknesses may be measured using the Optimas 3.0 imaging program (Optimas) and a Nikon scope (Nikon). These measurements may be used to determine the intima:media ratio (I/M). Statistical analysis may be performed using ANOVA with $p<0.005$.

Example 2

VEGF Binding Agents 9.10 Inhibition of VEGF-Mediated Tyrosine Phosphorylation and MAP Kinase Activation by GFB-116

In order to identify molecules that would bind vascular endothelial growth factor (VEGF), Flk-1/3T3 cell-based assay is used that relies on VEGF-stimulation of its receptor, Flk-1, tyrosine phosphorylation and subsequent MAP-kinase activation. The assay used herein identical to that used for PDGF, except that NIH 3T3 cells that overexpress Flk-1 are used. GFB-116, which has four identical loops with the sequence GKGK (SEQ ID NO. 10) is shown to be very potent and selective toward blocking the ability of VEGF to stimulate Flk-1 tyrosine phosphorylation and subsequent MAP-kinase activation as measured by phospho erk-1 and erk-2 also referred to in the Table as p42 and p44 (Table 4A). A preferred embodiment of the invention is a compound that binds to a vascular endothelial growth factor, of the general structure III (above) in which R is n-butyl, n-propyl, or benzyl, and X comprise covalently attached identical cyclic peptide loops wherein $R_1$, $R_2$, $R_3$, and $R_4$ are each amino acid side chains, as broadly defined above, that define a tetrapeptide sequence, wherein said tetrapeptide is covalently attached at the amino and carboxy termini of said tetrapeptide to 3-aminomethyl-5aminobenzamide linking group, and wherein said tetrapeptide sequence is GKGK (SEQ ID NO. 10), GDGY (SEQ ID NO. 6), or functionally related derivatives thereof.

Figure 12:
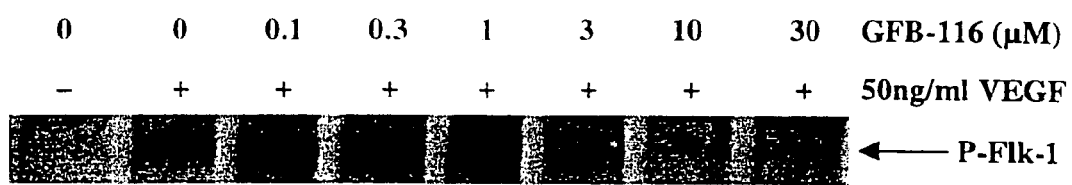
FIG. 12 illustrates the inhibition of VEGF-stimulated flk-1 tyrosine phosphorylation by GFB-116.
Figure 13:
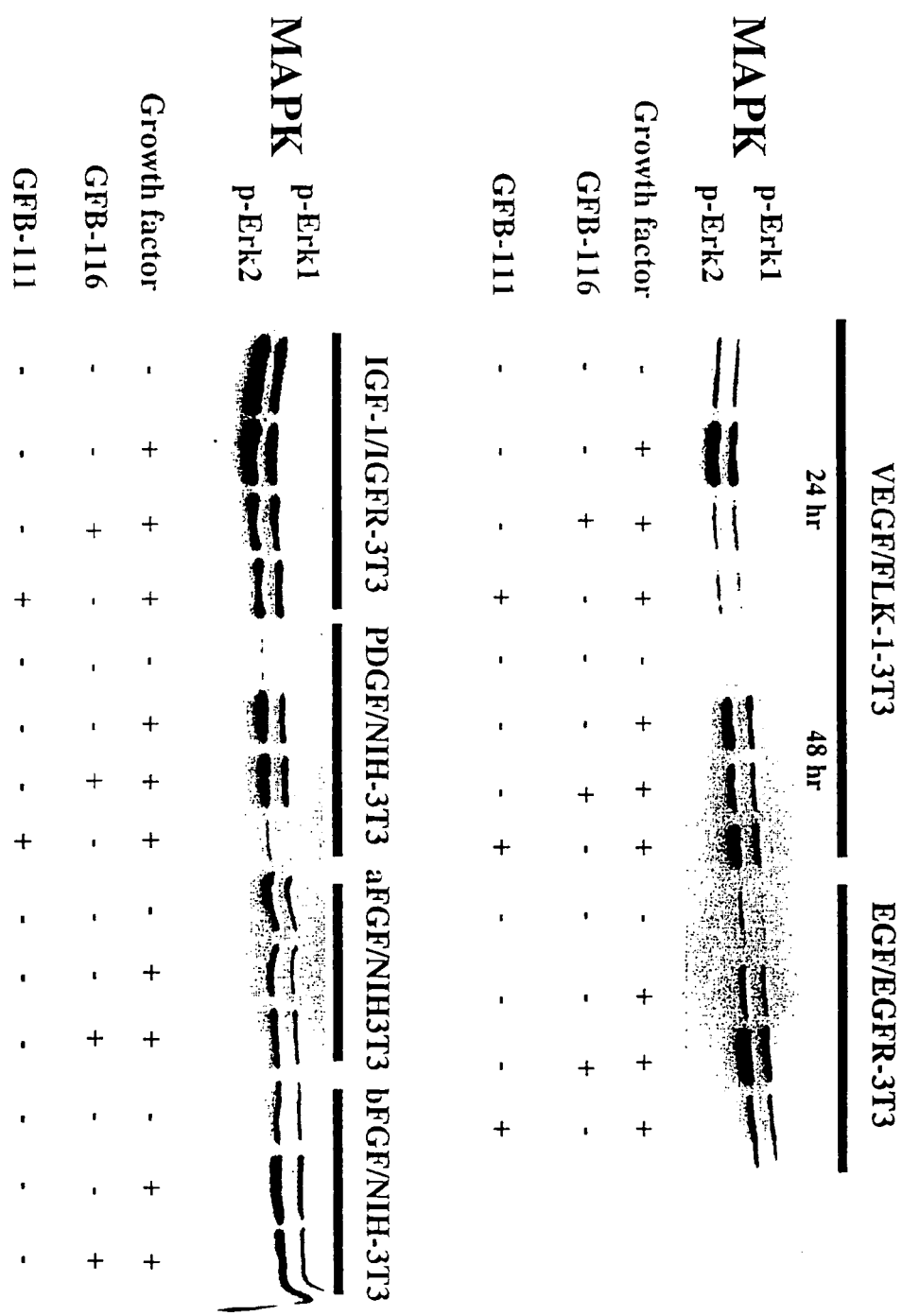
FIG. 13 illustrates selective inhibition of MAP kinase activation in vitro by GFB-116.
Figure 14:
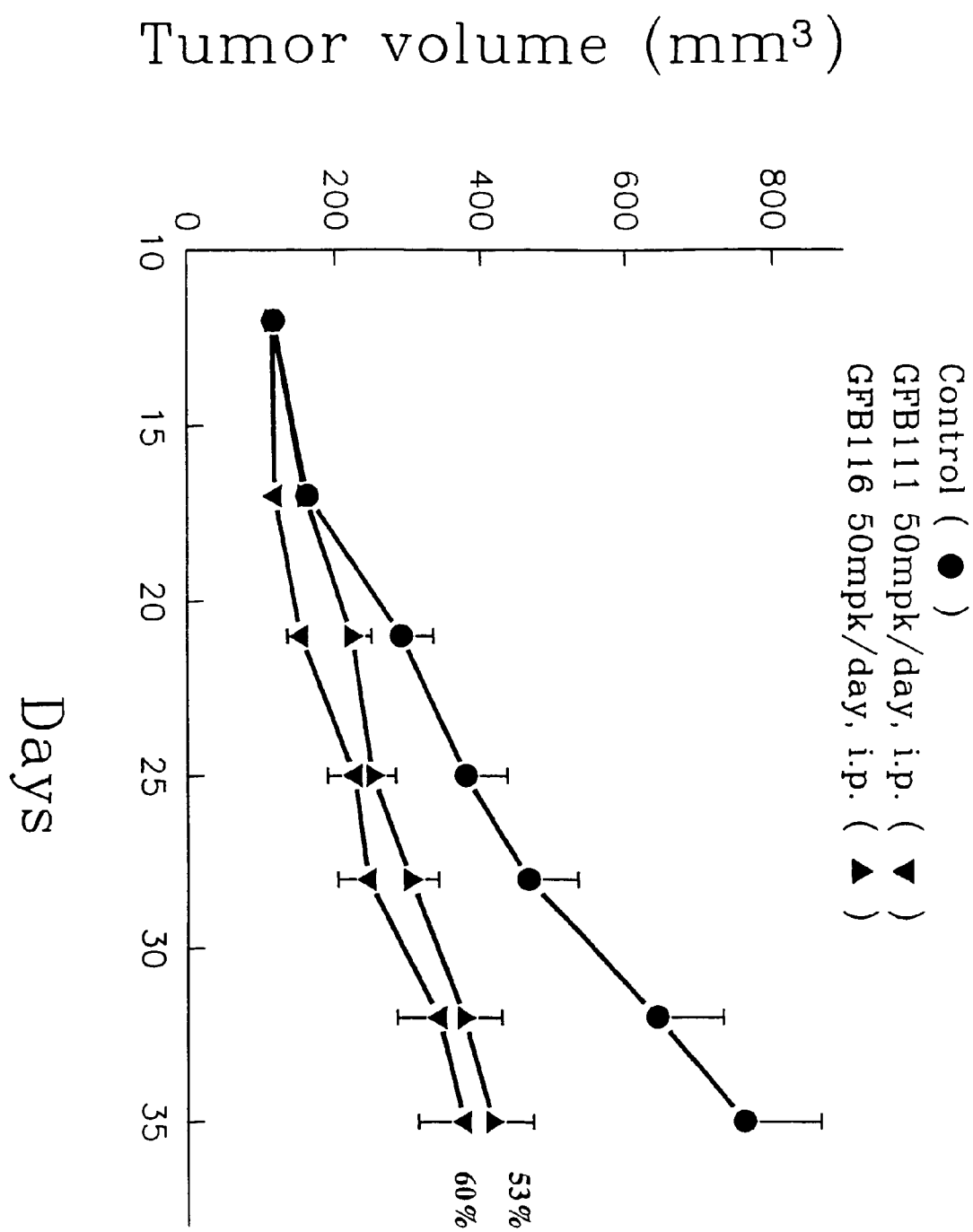
FIG. 14 illustrates inhibition of human tumor growth in nude mice by GFB-116.
Figure 15:
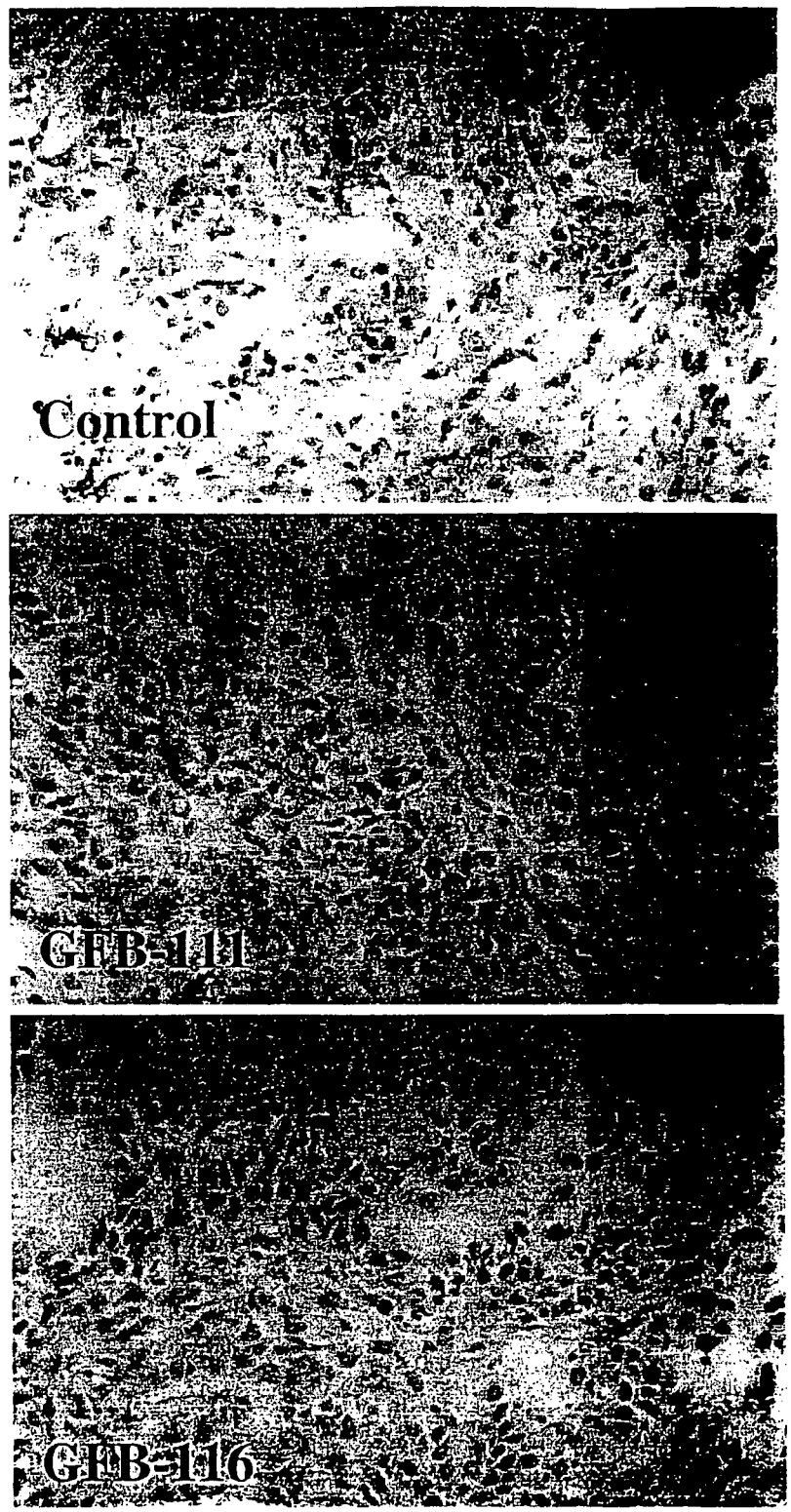
FIG. 15 illustrates inhibition of angiogenesis by GFB-116.
Figure 16:
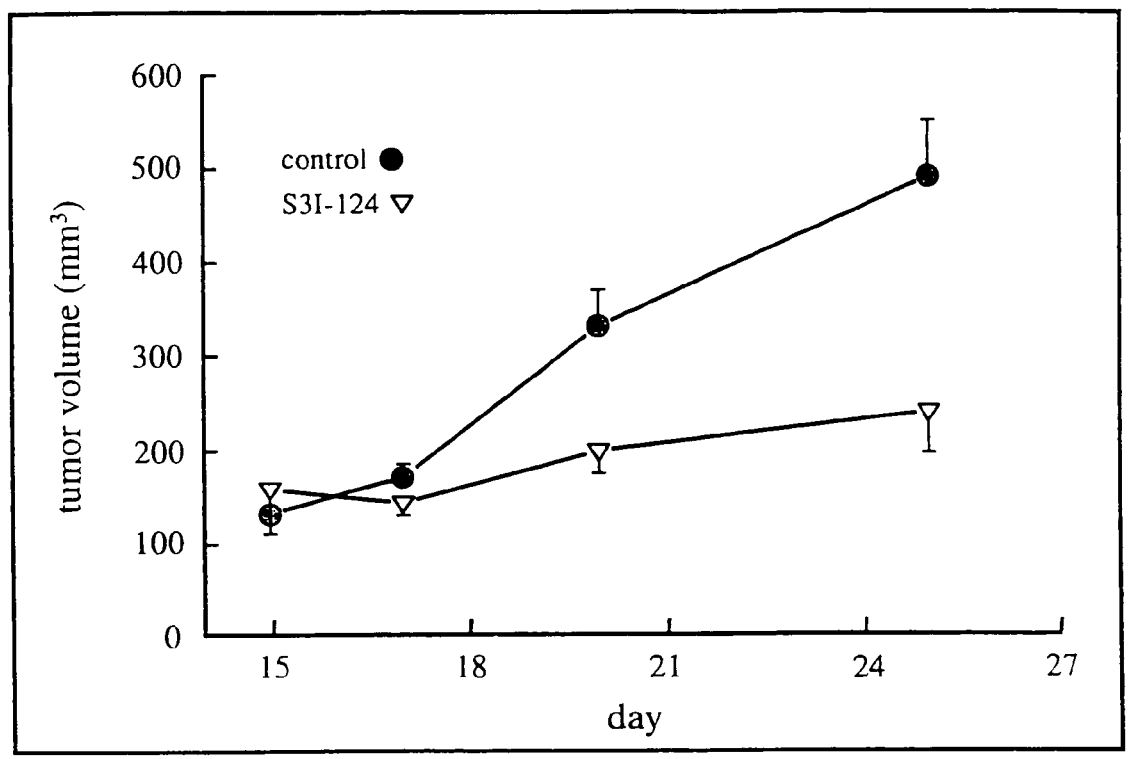
FIG. 16 illustrates inhibition of B-16 melanoma tumor growth in immune-competent mice by GFB 116.

Referring now to FIG. 12, GFB-116 inhibits VEGF-stimulated flk-1 tyrosine phosphorylation with an $IC_{50}$ value of 3 mM. In contrast, GFB-116 does not inhibit PDGF-stimulated PDGFR tyrosine phosphorylation, even at concentrations as high as 10 mM. This selectivity is further shown by administering GFB-116 to block VEGF-activation of the MAPKinases, Erk1 and Erk2, without affecting closely related growth factors (FIG. 13). Furthermore, GFB-111 inhibits PDGF-stimulated MAPKinase activation whereas GFB-116 does not (FIG. 13). The ability of GFB-116 to inhibit human tumor growth in nude mice is illustrated in FIG. 14, which shows that GFB-116 at 50 mg per Kg per day inhibits the growth of the human non-small cell lung carcinoma A-549 cell line in nude mice. Thus, GFB-116 is as potent as GFB-111 at inhibiting A-549 tumor growth (FIG. 15). Using factor VIII immunostaining on tumors extracted from the above-described nude mice, demonstrates that GFB-116 is also efficacious at inhibiting angiogenesis in vivo (FIG. 16). Quantification of the results by microvessel counting demonstrate that GFB-116 inhibits angiogenesis by 70% (Table 4B). Furthermore, GFB-116 was also effective at inhibiting the growth of B16-F10 melanoma in an immune-competent mouse model (FIG. 16). A549 cells are implanted s.c. under the flank of nude mice. When the tumors reach an average size of about 150 mm³, the animals are randomized and either treated with vehicle or S3I-124 (1 mg/kg/day) for 10 days. S3I-124 inhibits tumor growth by about 77%.

This embodiment of the present invention is a compound that binds to VEGF. Furthermore, the invention is directed to a composition for treating a subject, comprising the compound described immediately above, a pharmaceutically acceptable salt of this compound or combination thereof, in a pharmaceutically acceptable carrier.

A further embodiment of the invention is the administration of this composition to a patient having a condition comprising excess angiogenesis, a tumor or a combination thereof.

TABLE 4A

Inhibition of VEGF stimulated Flk-1 Tyrosine Phosphorylation and Signaling in Flk-1/3T3 by GFBs

Figure 7:
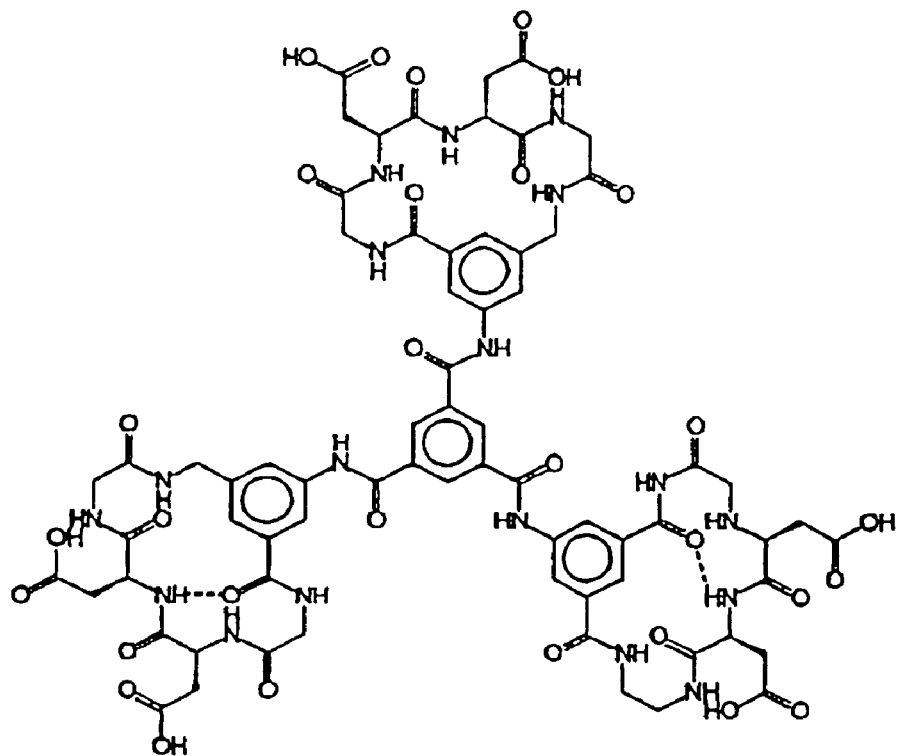
FIG. 7 illustrates the structure of GFB-114.

| Designation | Scaffold | R$_1$-R$_4$ sequence | (IC$_{50}$) Inhibition (μM) | | |
|---|---|---|---|---|---|
| | | | Flk-1-Y-P | p42 | p44 |
| GFB-101 | O4-Calix$^A$ | 4-GFGD (SEQ ID NO. 15) | >100 | >100 | >100 |
| GFB-102 | " | 4-GDFD (SEQ ID NO. 1) | 100 | >100 | >100 |
| GFB-103 | " | 4-GDGD (SEQ ID NO. 16) | | | |
| GFB-104 | O3-Calix$^A$ | 4-GDGD (SEQ ID NO. 16) | | | |
| GFB-105 | But-Calix$^A$ | 4-GDFD (SEQ ID NO. 1) | <10 | >100 | >100 |
| GFB-106 | " | 4-GDDD (SEQ ID NO. 2) | <10 | <10 | <10 |
| GFB-107 | " | 4-GDGD (SEQ ID NO. 16) | <10 | 100 | 100 |
| GFB-108 | " | 4-d-ADGD$^1$ (SEQ ID NO. 3) | 10 | 50 | 50 |
| GFB-109 | " | 4-GDLD (SEQ ID NO. 4) | | | |
| GFB-110 | " | 4-GDAD (SEQ ID NO. 5) | | | |
| GFB-111 | " | 4-GDGY (SEQ ID NO. 6) | 5 | 10 | 10 |
| GFB-112 | " | 4-ADGD (SEQ ID NO. 7) | <10 | 10 | 10 |
| GFB-113 | " | 4-GDSD (SEQ ID NO. 8) | <10 | 10 | 10 |
| GFB-114 | " | (4-) 8-acid (See FIG. 7) | | | |
| GFB-115 | | 4-GKGF (SEQ ID NO. 9) | | 5 | 5 |
| | | | | 10 | 10 |
| GFB-116 | | 4-GKGK (SEQ ID NO. 10) | 0.3 | 5 | 5 |
| GFB-117 | | 4-GDND (SEQ ID NO. 11) | | | |
| GFB-118 | | 4-D-2-NalDGD$^2$ (SEQ ID NO. 17) | | | |
| GFB-119 | | 4-PDGD (SEQ ID NO. 12) | | | |
| GFB-120 | " | 4-GDDG (SEQ ID NO. 13) | | | |
| GFB-121 | " | 4-d-AbuDGD$^3$ (SEQ ID NO. 18) | | | |
| GFB-122 | " | 4-GDDY (SEQ ID NO. 14) | | | |
| GFB-123 | " | 1-GDDG (SEQ ID NO. 13) | | | |
| GFB-124 | " | See FIG. 8 | | | |
| GFB-126 | " | 3 × GDDG (See FIG. 9) (SEQ ID NO. 13) | | | |
| GFB-127 | " | 2 × GDDG (See FIG. 9) (SEQ ID NO. 13) | | | |
| GFB-128 | " | DPM-2-GDGY (See FIG. 10) (SEQ ID NO. 6) | | | |
| GFB-129 | " | DPM-2-GDDD (See FIG. 10) (SEQ ID NO. 2) | | | |
| GFB-130 | " | DPM-2-GDDY (See FIG. 10) (SEQ ID NO. 14) | | | |
| GFB-131 | " | DPM-2-GDDG (See FIG. 10) (SEQ ID NO. 13) | | | |
| GFB-132 | But-Calix | 3-GDGY (SEQ ID NO. 6)-1-GDDG (SEQ ID NO. 13) (See FIG. 11) | | | |
| GFB-133 | " | 3-GDGY (SEQ ID NO. 6)-1-CO$_2$H (See FIG. 11) | | | |
| GFB-134 | " | 3-GDGY (SEQ ID NO. 6)-1-GDDY (SEQ ID NO. 14) (See FIG. 11) | | | |
| GFB-135 | " | 3-GDGY (SEQ ID NO. 6)-1-GDDD (SEQ ID NO. 2) (See FIG. 11) | | | |
| GFB-136 | " | 3-GDDD (SEQ ID NO. 2)-1-GDGY (SEQ ID NO. 6) (See FIG. 11) | | | |
| GFB-137 | " | 2-GDGY (SEQ ID NO. 6)-1-GDDG (SEQ ID NO. 13) (See FIG. 11) | | | |

$^A$The difference between GFB-101 through GFB-103 (04-Calix), GFB-104 (03-Calix), and the rest of the GFB compounds (But-Calix) is related to the structure of the calix tail. (Please refer to FIG. 6)

$^1$GFB-108: The "d" refers to D-amino acid, so d-ADGD is (D-Ala)-Asp-Gly-Asp SEQ ID NO. 3).

$^2$GFB-11*: D-2 Nal is structurally related to D-Phe. Instead of the phenyl ring in Phe, it has naphthelene ring linked through the 2-position.

$^3$GFB-121: d-Abu is D-aminobutyric acid. It has an ethyl group in the side chain while Ala has a methyl group in the side chain.

TABLE 4B

GFB-116 and GFB-111 Anti-angiogenic Activity in vivo

| Tumor | Group | Microvessel Count (Mean ± sd) | |
|---|---|---|---|
| | | 250X | 400X |
| A-549 | Control | 13.58 ± 4.44 | 9.52 ± 3.08 |
| | GFB-111 (50 mpk) | 5.68 ± 1.74 | 3.58 ± 1.01 |
| | GFB-116 (50 mpk) | 5.56 ± 1.75 | 3.46 ± 1.19 |

Example 3 aFGF Binding Agents 9.11 Inhibition of aFGF Stimulation of p42/p44 by Growth Factor Binding Agents The ability of growth factor binding agents in the library of growth factor binding agents to block an aFGF signal is measured by aFGF-stimulation of MAP kinase activation of p42 and p44 essentially as described above for VEGF. NIH 3T3 cells are used as the target cell. The growth factor binding molecules GFB-106, GFB-116, GFB-126, GFB-127, and GFB-133 are found to be very effective, see Table 5. A preferred embodiment of the invention is a compound that binds to acidic fibroblast growth factor, of the general structure III, in which R is n-butyl, n-propyl, or benzyl, and $X_1$, $X_2$, $X_3$, and $X_4$ optionally comprise covalently attached cyclic peptide loops of the general structure II, wherein $R_1$, $R_2$, $R_3$, and $R_4$ are each amino acid side chains that define a tetrapeptide sequence, wherein said tetrapeptide is covalently attached at the amino and carboxy termini of said tetrapeptide to a 3-aminomethyl-5-aminobenzamide linking group, and wherein said tetrapeptide sequence is as given, for example, in Table 5.

The present embodiment of the invention is directed to a compound that binds to a acidic fibroblast growth factor as described immediately above. Furthermore, the invention is directed to a composition for treating a subject comprising the compound described immediately above, a pharmaceutically acceptable salt, or combination thereof, in a pharmaceutically acceptable carrier. A further embodiment of the invention is a method of use of the therapeutic composition described immediately above in which the composition is administered to a subject suffering from a condition comprising undesired angiogenesis, a tumor or a combination thereof.

TABLE 5

Inhibition of aFGF stimulated FGFR Tyrosine Phosphorylation and Signaling in NIH 3T3 by GFBs

| Designation | Scaffold | $R_1$-$R_4$ sequence | ($IC_{50}$) Inhibition (μM) | | |
|---|---|---|---|---|---|
| | | | FGFR-Y-P | p42 | p44 |
| GFB-101 | O4-Calix[4] | 4-GFGD (SEQ ID NO. 15) | | ND | |
| GFB-102 | " | 4-GDFD (SEQ ID NO. 1) | | ND | |
| GFB-103 | " | 4-GDGD (SEQ ID NO. 16) | | ND | |
| GFB-104 | O3-Calix[4] | 4-GDGD (SEQ ID NO. 16) | ND | 2.5 | 0.7 |
| GFB-105 | But-Calix[4] | 4-GDFD (SEQ ID NO. 1) | ND | 66.4 | 75.7 |
| GFB-106 | " | 4-GDDD (SEQ ID NO. 2) | ND | 95.1 | 98.2 |
| GFB-107 | " | 4-GDGD (SEQ ID NO. 16) | ND | 57.3 | 59.7 |
| GFB-108 | " | 4-d-ADGD[1] (SEQ ID NO. 3) | ND | 67.8 | 80.1 |
| GFB-109 | " | 4-GDLD (SEQ ID NO. 4) | ND | 68.3 | 79.7 |
| GFB-110 | " | 4-GDAD (SEQ ID NO. 5) | ND | 76.1 | 85.2 |
| | | | | 93.0 | 98.9 |
| GFB-111 | " | 4-GDGY (SEQ ID NO. 6) | ND | 51.0 | 68.0 |
| | | | | 39.0 | 51.8 |
| GFB-112 | " | 4-ADGD (SEQ ID NO. 7) | ND | 59.7 | 62.9 |
| | | | | 40.2 | 39.6 |
| GFB-113 | " | 4-GDSD (SEQ ID NO. 8) | ND | 53.6 | 64.3 |
| GFB-114 | " | (4-) 8-acid (See FIG. 7) | ND | −8.7 | −16.9 |
| GFB-115 | " | 4-GKGF (SEQ ID NO. 9) | ND | −21.0 | −23.9 |
| GFB-116 | | 4-GKGK (SEQ ID NO. 10) | ND | 99.2 | 97.5 |
| | | | | 99.6 | 97.2 |
| | | | | 101.9 | 116.2 |
| | | | | 99.7 | 99.9 |
| | | | | 100.1 ± 1.2 | 102.7 ± 9.1 |
| GFB-117 | | 4-GDND (SEQ ID NO. 11) | ND | 63.4 | 80.8 |
| | | | | 67.6 | 84.3 |
| GFB-118 | | 4-D-2-NalDGD[2] (SEQ ID NO. 17) | ND | 20.6 | 30.5 |
| GFB-119 | | 4-PDGD (SEQ ID NO. 12) | ND | 62.6 | 78.9 |
| | | | | 72.1 | 81.7 |
| | | | | 47.8 | 58.1 |
| | | | | 60.8 ± 12.2 | 72.9 ± 12.9 |
| GFB-120 | " | 4-GDDG (SEQ ID NO. 13) | ND | 68.1 | 74.3 |
| GFB-121 | " | 4-d-AbuDGD[3] (SEQ ID NO. 18) | ND | 8.7 | 8.9 |
| GFB-122 | " | 4-GDDY (SEQ ID NO. 14) | ND | 57.3 | 71.6 |
| GFB-123 | " | 1-GDDG (SEQ ID NO. | ND | 11.4 | 12.5 |

TABLE 5-continued

Inhibition of aFGF stimulated FGFR Tyrosine Phosphorylation and Signaling in NIH 3T3 by GFBs

| Designation | Scaffold | $R_1$-$R_4$ sequence | ($IC_{50}$) Inhibition (µM) | | |
| --- | --- | --- | --- | --- | --- |
| | | | FGFR-Y-P | p42 | p44 |
| | | 13) | | | |
| GFB-124 | " | See FIG. 8 | ND | 0.3 | −1.7 |
| GFB-126 | " | 3 × GDDG (See FIG. 9) (SEQ ID NO. 13) | ND | 96.5 | 106.0 |
| GFB-127 | " | 2 × GDDG (See FIG. 9) (SEQ ID NO. 13) | ND | 97.5 | 107.4 |
| GFB-128 | " | DPM-2-GDGY (See FIG. 10) (SEQ ID NO. 6) | ND | 23.5 | 43.3 |
| GFB-129 | " | DPM-2-GDDD (See FIG. 10) (SEQ ID NO. 2) | ND | 11.3 | 3.2 |
| GFB-130 | " | DPM-2-GDDY (See FIG. 10) (SEQ ID NO. 14) | ND | 78.9 | 78.9 |
| GFB-131 | " | DPM-2-GDDG (See FIG. 10) (SEQ ID NO. 13) | ND | 33.4 | 44.1 |
| GFB-132 | But-Calix | 3-GDGY (SEQ ID NO. 6)-1-GDDG (SEQ ID NO. 13) (See FIG. 11) | ND | 48.2 | 50.2 |
| GFB-133 | " | 3-GDGY (SEQ ID NO. 6)-1-$CO_2H$ (See FIG. 11) | ND | 95.8 | 101.0 |
| GFB-134 | " | 3-GDGY (SEQ ID NO. 6)-1-GDDY (SEQ ID NO. 14) (See FIG. 11) | ND | 54.8 | 64.1 |
| GFB-135 | " | 3-GDGY (SEQ ID NO. 6)-1-GDDD (SEQ ID NO. 2) (See FIG. 11) | ND | 44.1 | 53.9 |
| GFB-136 | " | 3-GDDD (SEQ ID NO. 2)-1-GDGY (SEQ ID NO. 6) (See FIG. 11) | ND | 73.1 | 84.5 |
| GFB-137 | " | 2-GDGY (SEQ ID NO. 6)-1-GDDG (SEQ ID NO. 13) (See FIG. 11) | ND | 6.4 | 19.9 |

[A]The difference between GFB-101 through GFB-103 (04-Calix), GFB-104 (O3-Calix), and the rest of the GFB compounds (But-Calix) is related to the structure of the calix tail. (Please refer to FIG. 1.)
[1]GFB-108: The "d" refers to D-amino acid, so d-ADGD is (D-Ala)-Asp-Gly-Asp (SEQ ID NO. 3).
[2]GFB-118: D-2 Nal is structurally related to D-Phe. Instead of the phenyl ring in Phe, it has a naphthelene ring linked through the 2-position.
[3]GFB-121: d-Abu is D-aminobutyric acid. It has an ethyl group in the side chain while Ala has a methyl group in the side chain.

Example 4

IGF-1 Binding Agents 9.12 Inhibition of Insulin-like Growth Factor-1 (IGF-1) Mediated Tyrosine Phosphorylation and MAP Kinase Activation by GFB-126

The ability of the GFB library to block the ability of IGF-1 to stimulate the IFG-1 R tyrosine phosphorylation and MAP kinase activation is evaluated using the cell assay described above with IGF-R/3T3 cells as target cell. IFG-1R/3T3 cells are cells transfected with the IGF-R gene to overproduce IFG-1R. IFG-1R has been shown to be critical to survival of many human cancer cell types and for tumor progression. GFB-126 is found to be particularly effective in blocking IFG-1 action, see Table 6. A preferred embodiment of the invention is a compound that binds to an insulin-like growth factor-1, of the general structure III, wherein R is n-butyl, n-propyl, or benzyl, and $X_1$, $X_2$, $X_3$, and $X_4$ optionally comprise identical cyclic peptide loops of the general structure II, and wherein $R_1$, $R_2$, $R_3$, and $R_4$ are each amino acid side chains that define a tetrapeptide sequence, wherein said tetrapeptide is covalently attached at the amino and carboxy termini of said tetrapeptide to a 3-aminomethyl-5-aminobenzamide linking group.

This invention is also directed to a compound that binds to an insulin-like growth factor-1 as described immediately above. The invention is further directed to a composition for treating a subject, comprising administering the compound described immediately above, a pharmaceutically acceptable salt of this compound, or combination thereof, in a pharmaceutically acceptable carrier, and in which the subject suffers excess cellular proliferation, excess angiogenesis, a tumor, or a combination thereof.

TABLE 6

Inhibition of IGF-1 stimulated IGFR Tyrosine Phosphorylation and Signaling in IGFR/3T3 by GFB's

| | | | % Inhibition at 100 μM | | |
|---|---|---|---|---|---|
| Designation | Scaffold | R₁-R₄ sequence | IGF1R-Y-P | p42 | p44 |
| GFB-101 | O4-Calix[4] | 4-GFGD (SEQ ID NO. 15) | | ND | |
| GFB-102 | " | 4-GDFD (SEQ ID NO. 1) | | ND | |
| GFB-103 | " | 4-GDGD (SEQ ID NO. 16) | | ND | |
| GFB-104 | O3-Calix[4] | 4-GDGD (SEQ ID NO. 16) | −28.4 | −0.19 | 22.4 |
| GFB-105 | But-Calix[4] | 4-GDFD (SEQ ID NO. 1) | 1.3 | | |
| GFB-106 | " | 4-GDDD (SEQ ID NO. 2) | ND | | |
| GFB-107 | " | 4-GDGD (SEQ ID NO. 16) | ND | 57.3 | 59.7 |
| GFB-108 | " | 4-d-ADGD[1] (SEQ ID NO. 3) | ND | 67.8 | 80.1 |
| GFB-109 | " | 4-GDLD (SEQ ID NO. 4) | ND | 68.3 | 79.7 |
| GFB-110 | " | 4-GDAD (SEQ ID NO. 5) | 40.9 | 27.2 | 55.4 |
| | | | 32.4 | 8.6 | 47.1 |
| GFB-111 | " | 4-GDGY (SEQ ID NO. 6) | −12.4 | −18.4 | 10.7 |
| GFB-112 | " | 4-ADGD (SEQ ID NO. 7) | 0.6 | −7.6 | 30.4 |
| GFB-113 | " | 4-GDSD (SEQ ID NO. 8) | −18.9 | −31.4 | 18.7 |
| GFB-114 | " | (4-) 8-acid (See FIG. 7) | −28.9 | 43.6 | 76.8 |
| GFB-115 | | 4-GKGF (SEQ ID NO. 9) | −38.3 | −12.4 | 51.9 |
| GFB-116 | | 4-GKGK (SEQ ID NO. 10) | −149.2 | −29.8 | 25.2 |
| | | | −90.0 | 5.2 | 43.5 |
| GFB-117 | | 4-GDND (SEQ ID NO. 11) | 4.9 | 17.1 | 61.5 |
| GFB-118 | | 4-D-2-NalDGD[2] (SEQ ID NO. 17) | 1.5 | 16.4 | 55.2 |
| GFB-119 | | 4-PDGD (SEQ ID NO. 12) | 16.7 | 29.7 | 66.2 |
| GFB-120 | " | 4-GDDG (SEQ ID NO. 13) | 35.4 | 68.1 | 85.9 |
| GFB-121 | " | 4-d-AbuDGD[3] (SEQ ID NO. 18) | 33.8 | 28.3 | 62.1 |
| GFB-122 | " | 4-GDDY (SEQ ID NO. 14) | 38.4 | 33.6 | 66.6 |
| GFB-123 | " | 1-GDDG (SEQ ID NO. 13) | 24.2 | 26.7 | 62.4 |
| GFB-124 | " | See FIG. 8 | −9.5 | 3.0 | −20.4 |
| GFB-126 | " | 3 × GDDG (See FIG. 9) (SEQ ID NO. 13) | 51.7 | 63.9 | 71.2 |
| | | | 51.0 | 47.0 | 79.2 |
| GFB-127 | " | 2 × GDDG (See FIG. 9) (SEQ ID NO. 13) | 36.8 | 38.4 | 61.6 |
| | | | 31.8 | 27.2 | 74.4 |
| GFB-128 | " | DPM-2-GDGY (See FIG. 10) (SEQ ID NO. 6) | −12.0 | −6.1 | 38.2 |
| GFB-129 | " | DPM-2-GDDD (See FIG. 10) (SEQ ID NO. 2) | 3.4 | 2.8 | 33.4 |
| GFB-130 | " | DPM-2-GDDY (See FIG. 10) (SEQ ID NO. 14) | 22.7 | −19.7 | −17.5 |
| GFB-131 | " | DPM-2-GDDG (See FIG. 10) (SEQ ID NO. 13) | 30.2 | −6.2 | 20.0 |
| GFB-132 | But-Calix | 3-GDGY (SEQ ID NO. 6)-1-GDDG (SEQ ID NO. 13) (See FIG. 11) | 30.2 | 11.0 | 39.4 |
| GFB-133 | " | 3-GDGY (SEQ ID NO. 6)-1-CO₂H (See FIG. 11) | ND | ND | ND |
| GFB-134 | " | 3-GDGY (SEQ ID NO. 6)-1-GDDY (SEQ ID NO. 14) (See FIG. 11) | 16.8 | 4.9 | 53.5 |
| GFB-135 | " | 3-GDGY (SEQ ID NO. 6)-1-GDDD (SEQ ID NO. 2) (See FIG. 11) | 16.2 | 0.8 | 46.1 |
| GFB-136 | " | 3-GDDD (SEQ ID NO. 2)-1-GDGY (SEQ ID NO. 6) (See FIG. 11) | 40.6 | 15.0 | 59.559.5 |

TABLE 6-continued

Inhibition of IGF-1 stimulated IGFR Tyrosine Phosphorylation and Signaling in IGFR/3T3 by GFB's

| | | | % Inhibition at 100 μM | | |
|---|---|---|---|---|---|
| Designation | Scaffold | $R_1$-$R_4$ sequence | IGF1R-Y-P | p42 | p44 |
| GFB-137 | " | 2-GDGY (SEQ ID NO. 6)-1-GDDG (SEQ ID NO. 13) (See FIG. 11) | 36.0 | 5.9 | 38.2 |

[A]The difference between GFB-101 through GFB-103 (O4-Calix), GFB-104 (O3-Calix), and the rest of the GFB compounds (But-Calix) is related to the structure of the calix tail. (Please refer to FIG. 6.)
[1]GFB-108: The "d" refers to D-amino acid, so d-ADGD is (D-Ala)-Asp-Gly-Asp (SEQ ID NO. 3).
[2]GFB-118: D-2 Nal is structurally related to D-Phe. Instead of the phenyl ring in Phe, it has a naphthelene ring linked through the 2-position.
[3]GFB-121: d-Abu is D-aminobutyric acid. It has an ethyl group in the side chain while Ala has a methyl group in the side chain.

The above examples have been depicted solely for the purpose of exemplification and are not intended to restrict the scope or embodiments of the invention. Other embodiments not specifically described should be apparent to those of ordinary skill in the art. Such other embodiments are considered to fall, nevertheless, within the scope and spirit of the present invention. Thus, the invention is properly limited solely by the claims that follow.

What is claimed is:

1. A method of binding a platelet derived growth factor in a subject having a condition associated with said platelet derived growth factor, comprising administering to the subject an effective amount of a growth factor binding compound of the general structure:

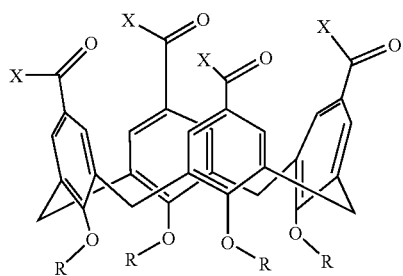

or a pharmaceutically acceptable salt thereof, wherein R is n-butyl, n-propyl, benzyl, ($C_1$-$C_{12}$) alkyl, ($C_7$-$C_{18}$) aralkyl, ($C_6$-$C_{18}$) aryl, ($C_1$-$C_{12}$) alkenyl, ($C_7$-$C_{18}$) aralkenyl, or ($C_1$-$C_{12}$) alkylether, and X are independently cyclic peptide loops of the general structure:

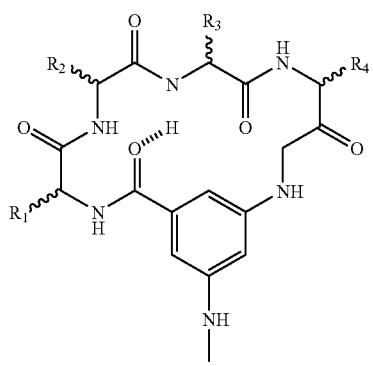

wherein $R_1$, $R_2$, $R_3$, and $R_4$ are each amino acid side chains that define a tetrapeptide, wherein said tetrapeptide is covalently attached at the amino and carboxy termini of said tetrapeptide to a 3-aminomethyl-5-aminobenzamide linking group, and wherein said tetrapeptide is GDAD (SEQ ID NO. 5), GDGY (SEQ ID NO. 6), GDDG (SEQ ID NO. 13), or GDDY (SEQ ID NO. 14).

2. The method of claim 1, wherein the growth factor binding compound is administered to the subject with a pharmaceutically acceptable carrier.

3. The method of claim 1, wherein the subject is human.

4. A method of inhibiting angiogenesis in a subject wherein the angiogenesis is signaled through the platelet derived growth factor receptor, comprising administering to the subject an effective amount of a growth factor binding compound of the general structure:

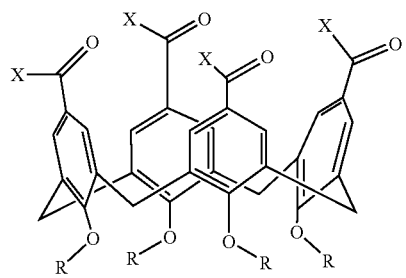

or a pharmaceutically acceptable salt thereof, wherein R is n-butyl, n-propyl, benzyl, ($C_1$-$C_{12}$) alkyl, ($C_7$-$C_{18}$) aralkyl, ($C_6$-$C_{18}$) aryl, ($C_1$-$C_{12}$) alkenyl, ($C_7$-$C_{18}$) aralkenyl, or ($C_1$-$C_{12}$) alkylether, and X are independently cyclic peptide loops of the general structure:

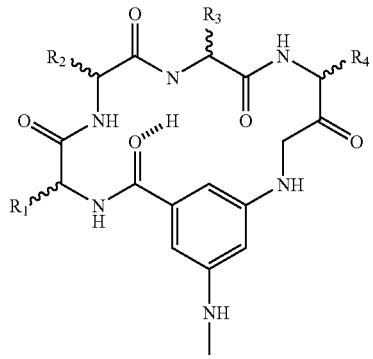

wherein $R_1$, $R_2$, $R_3$, and $R_4$ are each amino acid side chains that define a tetrapeptide, wherein said tetrapeptide is covalently attached at the amino and carboxy termini of said tetrapeptide to a 3-aminomethyl-5-aminobenzamide linking group, and wherein said tetrapeptide is GDAD (SEQ ID NO. 5), GDGY (SEQ ID NO. 6), GDDG (SEQ ID NO. 13), or GDDY (SEQ ID NO. 14), wherein the subject is suffering from a disease comprising excess angiogenesis.

5. The method of claim 4, wherein the subject has a solid tumor and said administering inhibits growth of the solid tumor.

6. The method of claim 5, wherein the tumor expresses elevated amounts of platelet derived growth factor prior to said administering.

7. The method of claim 4, wherein the subject is human.

8. The method of claim 4, wherein the growth factor binding compound is administered to the subject with a pharmaceutically acceptable carrier.

9. A method of binding a vascular endothelial growth factor in a subject having a condition associated with said vascular endothelial growth factor, comprising administering to the subject an effective amount of a growth factor binding compound of the general structure:

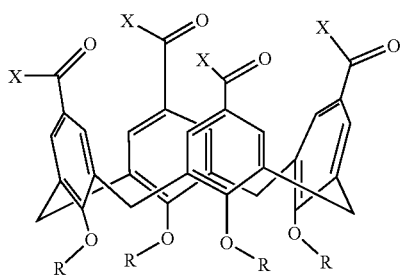

or a pharmaceutically acceptable salt thereof, wherein R is n-butyl, n-propyl, benzyl, ($C_1$-$C_{12}$) alkyl, ($C_7$-$C_{18}$) aralkyl, ($C_6$-$C_{18}$) aryl, ($C_1$-$C_{12}$) alkenyl, ($C_7$-$C_{18}$) aralkenyl, or($C_1$-$C_{12}$) alkylether, and X are independently cyclic peptide loops of the general structure:

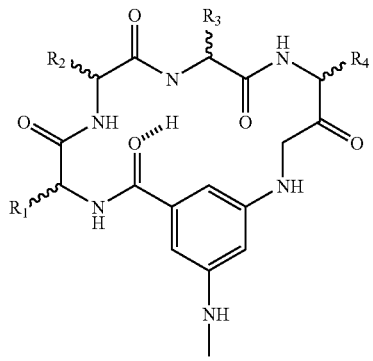

wherein $R_1$, $R_2$, $R_3$, and $R_4$ are each amino acid side chains that define a tetrapeptide, wherein said tetrapeptide is covalently attached at the amino and carboxy termini of said tetrapeptide to a 3-aminomethyl-5-aminobenzamide linking group, and wherein said tetrapeptide is GDGY (SEQ ID NO. 6) or GKGK (SEQ ID NO. 10).

10. The method of claim 9, wherein the growth factor binding compound is administered to the subject with a pharmaceutically acceptable carrier.

11. The method of claim 9, wherein the subject is human.

12. A method of binding an acidic fibroblast growth factor in a subject having a condition associated with said acidic fibroblast growth factor, comprising administering to the subject an effective amount of a growth factor binding compound of the general structure:

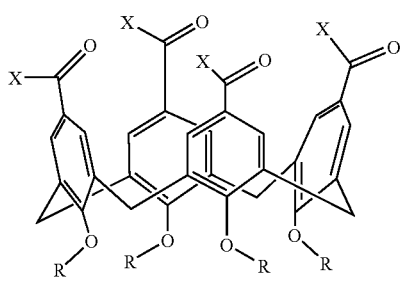

or a pharmaceutically acceptable salt thereof, wherein R is n-butyl, n-propyl, benzyl, ($C_1$-$C_{12}$) alkyl, ($C_7$-$C_{18}$) aralkyl, ($C_6$-$C_{18}$) aryl, ($C_1$-$C_{12}$) alkenyl, ($C_7$-$C_{18}$) aralkenyl, or ($C_1$-$C_{12}$) alkylether, and X are independently cyclic peptide loops of the general structure:

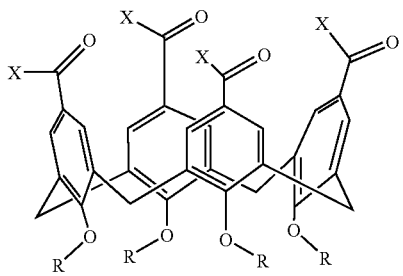

wherein $R_1$, $R_2$, $R_3$, and $R_4$ are each amino acid side chains that define a tetrapeptide, wherein said tetrapeptide is covalently attached at the amino and carboxy termini of said tetrapeptide to a 3-aminomethyl-5-aminobenzamide linking group, and wherein said tetrapeptide is from GDDD (SEQ ID NO. 2), GDAD (SEQ ID NO. 5), GDGY (SEQ ID NO. 6), GKGK (SEQ ID NO. 10), or GDDG (SEQ ID NO. 13).

13. The method of claim 12, wherein the growth factor binding compound is administered to the subject with a pharmaceutically acceptable earner.

14. The method of claim 12, wherein the subject is human.

15. A method of binding an insulin-like growth factor-1 in a subject having a condition associated with said insulin-like growth factor-1 , comprising administering to the subject an effective amount of a growth factor binding compound of the general structure:

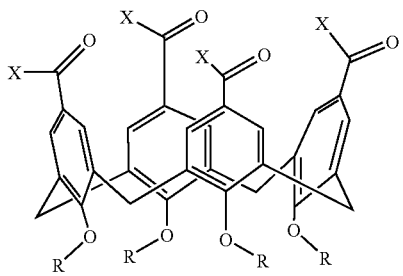

or a pharmaceutically acceptable salt thereof, wherein R is n-butyl, n-propyl, benzyl, ($C_1$-$C_{12}$) alkyl, ($C_7$-$C_{18}$) aralkyl, ($C_6$-$C_{18}$) aryl, ($C_1$-$C_{12}$) alkenyl, ($C_7$-$C_{18}$) aralkenyl, or ($C_1$-$C_{12}$) alkylether, and X are independently cyclic peptide loops of the general structure:

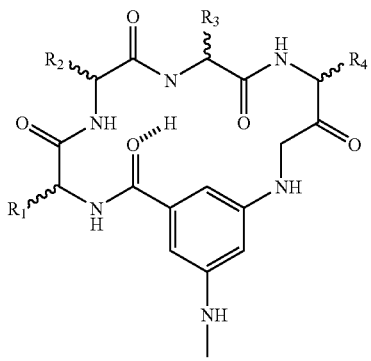

wherein $R_1$, $R_2$, $R_3$, and $R_4$ are each amino acid side chains that define a tetrapeptide, wherein said tetrapeptide is covalently attached at the amino and carboxy termini of said tetrapeptide to a 3-aminomethyl-5-aminobenzamide linking group, and wherein said tetrapeptide is GDAD (SEQ ID NO. 5) or GDDG (SEQ ID NO. 13).

16. The method of claim 15, wherein the growth factor binding compound is administered to the subject with a pharmaceutically acceptable carrier.

17. The method of claim 15, wherein the subject is human.

18. A method of inhibiting angiogenesis in a subject wherein the angiogenesis is signaled through the vascular endothelial growth factor receptor, comprising administering to the subject an effective amount of a growth factor binding compound of the general structure:

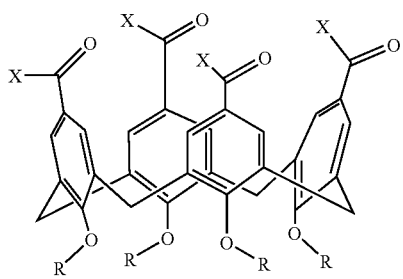

or a pharmaceutically acceptable salt thereof, wherein R is n-butyl, n-propyl, benzyl, ($C_1$-$C_{12}$) alkyl, ($C_7$-$C_{18}$) aralkyl, ($C_6$-$C_{18}$) aryl, ($C_1$-$C_{12}$) alkenyl, ($C_7$-$C_{18}$) aralkenyl, or ($C_1$-$C_{12}$) alkylether, and X are independently cyclic peptide loops of the general structure:

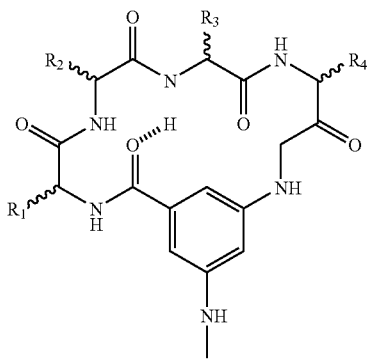

wherein $R_1$, $R_2$, $R_3$, and $R_4$ are each amino acid side chains that define a tetrapeplide, wherein said tetrapeptide is covalently attached at the amino and carboxy termini of said tetrapeptide to a 3-aminomethyl-5-aminobenzamide linking group, and wherein said tetrapeptide is GDGY (SEQ ID NO. 6) or GKGK (SEQ ID NO. 10), wherein the subject is suffering from a disease comprising excess angiogenesis.

19. The method of claim 18, wherein the subject has a solid tumor and said administering inhibits growth of the solid tumor.

20. The method of claim 18, wherein the subject is human.

21. The method of claim 18, wherein the growth factor binding compound is administered to the subject with a pharmaceutically acceptable carrier.

22. A method of inhibiting angiogenesis in a subject wherein the angiogenesis is signaled through the acidic fibroblast growth factor receptor, comprising administering to the subject an effective amount of a growth factor binding compound of the general structure:

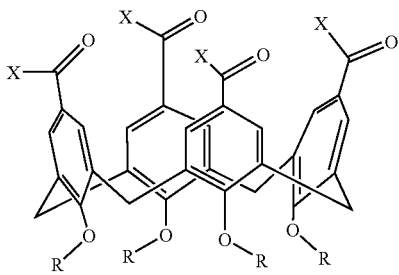

or a pharmaceutically acceptable salt thereof, wherein R is n-butyl, n-propyl, benzyl, ($C_1$-$C_{12}$) alkyl, ($C_7$-$C_{18}$) aralkyl, ($C_6$-$C_{18}$) aryl, ($C_1$-$C_{12}$) alkenyl, ($C_7$-$C_{18}$) aralkenyl, or($C_1$-$C_{12}$)alkylether, and X are independently cyclic peptide loops of the general structure:

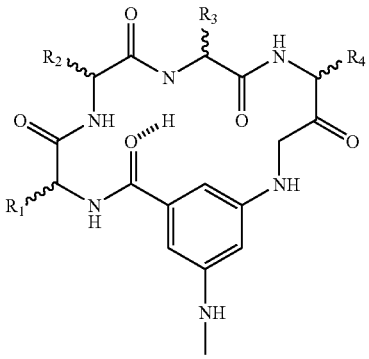

wherein $R_1$, $R_2$, $R_3$, and $R_4$ are each amino acid side chains that define a tetrapeptide, wherein said tetrapeptide is covalently attached at the amino and carboxy termini of said tetrapeptide to a 3-aminomethyl-5-aminobenzamide linking group, and wherein said tetrapeptide is GDDD (SEQ ID NO. 2), GDAD (SEQ ID NO. 5), GDGY (SEQ ID NO. 6), GKGK (SEQ ID NO. 10), or GDDG (SEQ ID NO. 13), wherein the subject is suffering from a disease comprising excess angiogenesis.

23. The method of claim 22, wherein the subject has a solid tumor and said administering inhibits growth of the solid tumor.

24. The method of claim 22, wherein the subject is human.

25. The method of claim 22, wherein the growth factor binding compound is administered to the subject with a pharmaceutically acceptable carrier.

26. A method of inhibiting angiogenesis ma subject wherein the angiogenesis is signaled through the insulin-like growth factor-1 receptor, comprising administering to the subject an effective amount of a growth factor binding compound of the general structure:

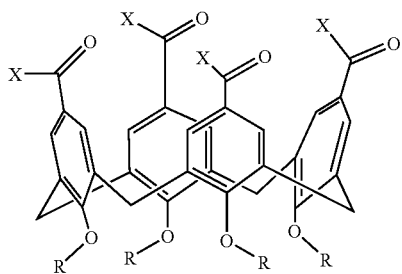

or a pharmaceutically acceptable salt thereof, wherein R is n-butyl, n-propyl, benzyl, ($C_1$-$C_{12}$) alkyl, ($C_7$-$C_{18}$) aralkyl, ($C_6$-$C_{18}$) aryl, ($C_1$-$C_{12}$) alkenyl, ($C_7$-$C_{18}$) aralkenyl, or ($C_1$-$C_{12}$) alkylether, and X are independently cyclic peptide loops of the general structure:

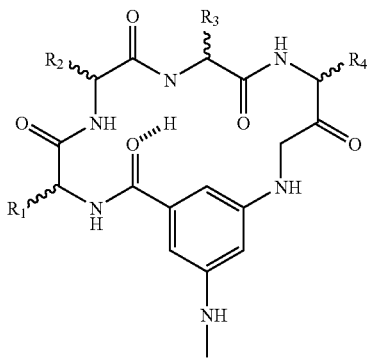

wherein $R_1$, $R_2$, $R_3$, and $R_4$ are each amino acid side chains that define a tetrapeptide, wherein said tetrapeptide is covalently attached at the amino and carboxy termini of said tetrapeptide to a 3-aminomethyl-5-aminobenzamide linking group, and wherein said tetrapeptide is GDAD (SEQ ID NO. 5) or GDDG (SEQ ID NO. 13), wherein the subject is suffering from a disease comprising excess angiogenesis.

27. The method of claim 26, wherein the subject has a solid tumor and said administering inhibits growth of the solid tumor.

28. The method of claim 26, wherein the subject is human.

29. The method of claim 26, wherein the growth factor binding compound is administered to the subject with a pharmaceutically acceptable carrier.

30. The method of claim 1, wherein said condition is a solid tumor.

31. The method of claim 9, wherein said condition is a solid tumor.

32. The method of claim 12, wherein said condition is a solid tumor.

33. The method of claim 15, wherein said condition is a solid tumor.

34. The method of claim 1, wherein said condition is cellular proliferation.

35. The method of claim 9, wherein said condition is cellular proliferation.

36. The method of claim 12, wherein said condition is cellular proliferation.

37. The method of claim 15, wherein said condition is cellular proliferation.

* * * * *

UNITED STATES PATENT AND TRADEMARK OFFICE
CERTIFICATE OF CORRECTION

PATENT NO. : 7,632,805 B2
APPLICATION NO. : 11/226112
DATED : December 15, 2009
INVENTOR(S) : Said M. Sebti et al.

It is certified that error appears in the above-identified patent and that said Letters Patent is hereby corrected as shown below:

Column 12
Line 30, "IGF-R" should read --IGF-1R--.

Column 17
Lines 20-21, "GFB-111, [I]-PDGF-BB" should read --GFB-111, [$^{125}$I]-PDGF-BB--.

Column 21
Line 67, "$^2$GFB-11*: D-2 NaI" should read --$^2$GFB-118: D-2 Nal--.

Column 37
Lines 51-52, "5-aminobenzarnide" should read --5-aminobenzamide--.

Column 42
Line 24, "or($C_1$-$C_{12}$)alkylether" should read --or ($C_1$-$C_{12}$) alkylether--.

Line 62, "angiogenesis ma subject" should read --angiogenesis in a subject--.

Column 44
Lines 4-5, "5-aminohenzamide" should read --5-aminobenzamide--.

Signed and Sealed this

Tenth Day of August, 2010

David J. Kappos
*Director of the United States Patent and Trademark Office*

```
SEQUENCE LISTING

<160> NUMBER OF SEQ ID NOS: 18

<210> SEQ ID NO 1
<211> LENGTH: 4
<212> TYPE: PRT
<213> ORGANISM: Artificial Sequence
<220> FEATURE:
<223> OTHER INFORMATION: Tetra-peptide used to create compounds
      designated GFB-102 and GFB-105.

<400> SEQUENCE: 1

Gly Asp Phe Asp
1

<210> SEQ ID NO 2
<211> LENGTH: 4
<212> TYPE: PRT
<213> ORGANISM: Artificial Sequence
<220> FEATURE:
<223> OTHER INFORMATION: Tetra-peptide used to create compounds
      designated GFB-106, GFB-129, GFB-135, and GFB-136.

<400> SEQUENCE: 2

Gly Asp Asp Asp
1

<210> SEQ ID NO 3
<211> LENGTH: 4
<212> TYPE: PRT
<213> ORGANISM: Artificial Sequence
<220> FEATURE:
<223> OTHER INFORMATION: Tetra-peptide used to create compound
      designated GFB-108.
<220> FEATURE:
<221> NAME/KEY: MISC_FEATURE
<222> LOCATION: (1)..(1)
<223> OTHER INFORMATION: Alanine is in the D conformation

<400> SEQUENCE: 3

Ala Asp Gly Asp
```

-continued

```
<210> SEQ ID NO 4
<211> LENGTH: 4
<212> TYPE: PRT
<213> ORGANISM: Artificial Sequence
<220> FEATURE:
<223> OTHER INFORMATION: Tetra-peptide used to create compound
      designated GFB-109.

<400> SEQUENCE: 4

Gly Asp Leu Asp
1

<210> SEQ ID NO 5
<211> LENGTH: 4
<212> TYPE: PRT
<213> ORGANISM: Artificial Sequence
<220> FEATURE:
<223> OTHER INFORMATION: Tetra-peptide used to create compound
      designated GFB-110.

<400> SEQUENCE: 5

Gly Asp Ala Asp
1

<210> SEQ ID NO 6
<211> LENGTH: 4
<212> TYPE: PRT
<213> ORGANISM: Artificial Sequence
<220> FEATURE:
<223> OTHER INFORMATION: Tetra-peptide used to create compounds
      designated GFB-111, GFB-128, GFB-132, GFB-133, GFB-134, GFB-135,
      GFB-136, and GFB-137.

<400> SEQUENCE: 6

Gly Asp Gly Tyr
1

<210> SEQ ID NO 7
<211> LENGTH: 4
<212> TYPE: PRT
<213> ORGANISM: Artificial Sequence
<220> FEATURE:
<223> OTHER INFORMATION: Tetra-peptide used to create compound
      designated GFB-112.

<400> SEQUENCE: 7

Ala Asp Gly Asp
1

<210> SEQ ID NO 8
<211> LENGTH: 4
<212> TYPE: PRT
<213> ORGANISM: Artificial Sequence
<220> FEATURE:
<223> OTHER INFORMATION: Tetra-peptide used to create compound
      designated GFB-113.

<400> SEQUENCE: 8

Gly Asp Ser Asp
1

<210> SEQ ID NO 9
<211> LENGTH: 4
<212> TYPE: PRT
<213> ORGANISM: Artificial Sequence
<220> FEATURE:
```

```
<223> OTHER INFORMATION: Tetra-peptide used to create compound
      designated GFB-115.

<400> SEQUENCE: 9

Gly Lys Gly Phe
1

<210> SEQ ID NO 10
<211> LENGTH: 4
<212> TYPE: PRT
<213> ORGANISM: Artificial Sequence
<220> FEATURE:
<223> OTHER INFORMATION: Tetra-peptide used to create compound
      designated GFB-116.

<400> SEQUENCE: 10

Gly Lys Gly Lys
1

<210> SEQ ID NO 11
<211> LENGTH: 4
<212> TYPE: PRT
<213> ORGANISM: Artificial Sequence
<220> FEATURE:
<223> OTHER INFORMATION: Tetra-peptide used to create compound
      designated GFB-117.

<400> SEQUENCE: 11

Gly Asp Asn Asp
1

<210> SEQ ID NO 12
<211> LENGTH: 4
<212> TYPE: PRT
<213> ORGANISM: Artificial Sequence
<220> FEATURE:
<223> OTHER INFORMATION: Tetra-peptide used to create compound
      designated GFB-119.

<400> SEQUENCE: 12

Pro Asp Gly Asp
1

<210> SEQ ID NO 13
<211> LENGTH: 4
<212> TYPE: PRT
<213> ORGANISM: Artificial Sequence
<220> FEATURE:
<223> OTHER INFORMATION: Tetra-peptide used to create compounds
      designated GFB-120, GFB-123, GFB-126, GFB-127, GFB-131, GFB-132,
      and GFB-137.

<400> SEQUENCE: 13

Gly Asp Asp Gly
1

<210> SEQ ID NO 14
<211> LENGTH: 4
<212> TYPE: PRT
<213> ORGANISM: Artificial Sequence
<220> FEATURE:
<223> OTHER INFORMATION: Tetra-peptide used to create compounds
      designated GFB-122, GFB-130, and GFB-134.

<400> SEQUENCE: 14

Gly Asp Asp Tyr
1
```

```
<210> SEQ ID NO 15
<211> LENGTH: 4
<212> TYPE: PRT
<213> ORGANISM: Artificial Sequence
<220> FEATURE:
<223> OTHER INFORMATION: Tetra-peptide used to create compound
      designated GFB-101.

<400> SEQUENCE: 15

Gly Phe Gly Asp
1

<210> SEQ ID NO 16
<211> LENGTH: 4
<212> TYPE: PRT
<213> ORGANISM: Artificial Sequence
<220> FEATURE:
<223> OTHER INFORMATION: Tetra-peptide used to create compounds
      designated GFB-103, GFB-104, and GFB-107.

<400> SEQUENCE: 16

Gly Asp Gly Asp
1

<210> SEQ ID NO 17
<211> LENGTH: 4
<212> TYPE: PRT
<213> ORGANISM: Artificial Sequence
<220> FEATURE:
<223> OTHER INFORMATION: Tetra-peptide used to create compound
      designated GFB-118.
<220> FEATURE:
<221> NAME/KEY: MISC_FEATURE
<222> LOCATION: (1)..(1)
<223> OTHER INFORMATION: Xaa = D-2 Nal. Structurally related to D-Phe,
      but instead of phenyl ring in Phe, it has a naphthelene ring
      linked at the 2-position.

<400> SEQUENCE: 17

Xaa Asp Gly Asp
1

<210> SEQ ID NO 18
<211> LENGTH: 4
<212> TYPE: PRT
<213> ORGANISM: Artificial Sequence
<220> FEATURE:
<223> OTHER INFORMATION: Tetra-peptide used to create compound
      designated GFB-121.
<220> FEATURE:
<221> NAME/KEY: MISC_FEATURE
<222> LOCATION: (1)..(1)
<223> OTHER INFORMATION: Xaa = dAbu. D-aminobutyric acid has an ethyl
      group in the side chain while Ala has a methyl group in the side
      chain.

<400> SEQUENCE: 18

Xaa Asp Gly Asp
1
```